(12) United States Patent
Duprat et al.

(10) Patent No.: US 6,309,855 B1
(45) Date of Patent: *Oct. 30, 2001

(54) FAMILY OF MAMMALIAN POTASSIUM CHANNELS, THEIR CLONING AND THEIR USE, ESPECIALLY FOR THE SCREENING OF DRUGS

(75) Inventors: Fabrice Duprat, Vallauris; Florian Lesage, Paris; Michel Fink, La Bocca; Michel Lazdunski, Nice, all of (FR)

(73) Assignee: Centre National de la Recherche (CNRS) (FR)

(*) Notice: Subject to any disclaimer, the term of this patent is extended or adjusted under 35 U.S.C. 154(b) by 0 days.

This patent is subject to a terminal disclaimer.

(21) Appl. No.: 09/144,914

(22) Filed: Sep. 1, 1998

Related U.S. Application Data

(63) Continuation-in-part of application No. 08/749,816, filed on Nov. 15, 1996, now Pat. No. 6,013,470.
(60) Provisional application No. 60/095,234, filed on Aug. 4, 1998.

(30) Foreign Application Priority Data

Feb. 8, 1996 (FR) .................................................. 96 01565

(51) Int. Cl.[7] .......................... C12P 21/06; C12N 15/00; C12N 15/63; C07H 21/02

(52) U.S. Cl. ...................... 435/69.1; 435/320.1; 435/325; 514/44; 536/23.5; 536/23.4; 536/23.1; 536/24.1

(58) Field of Search ................................ 435/69.1, 320.1, 435/325; 536/23.1, 23.4, 23.5, 24.1; 514/44

(56) References Cited

PUBLICATIONS

Kubo et al. Nature. vol. 362, 127–131, 1993.*
Lesage et al. EMBO J. vol. 15(5), 1004–1011, Mar. 1, 1996.*
Duprat et al. EMBO J. vol. 16(17), 5464–5471, Sep. 1, 1997.*

* cited by examiner

*Primary Examiner*—Geetha P. Bansal
(74) *Attorney, Agent, or Firm*—Schnader Harrison Segal & Lewis LLP

(57) ABSTRACT

This invention relates to a new member of a recently recognized TWIK potassium[+]channel family, herein identified as TASK, for TWIK-related acid-sensitive $K^+$ channel. This is the first cloned mammalian channel that produces $K^+$ currents that possesses all the characteristics of background conductances. The invention also relates to various constructs including the TASK or related human potassium channel family, and their uses.

13 Claims, 18 Drawing Sheets

```
                                            gggcaggaagacggcgctgcccggaggagc  -153
gggcgggcgggcgcgcggggggagcgggcggcgggcgggagccaggcccgggcgggggcgggggcggcggggccag  -77
aagaggcggcgggccgcgctccggccggtctgcggcgttggccttggcttttggcggcggcggtggagaag      -1
```

| | | | | | | | | | | | | | | | | | | | |
|---|---|---|---|---|---|---|---|---|---|---|---|---|---|---|---|---|---|---|---|
| ATG | CTG | CAG | TCC | CTG | GCC | GGC | AGC | TCG | TGC | GTG | CGC | CTG | GTG | GAG | CGG | CAC | CGC | TCG | 57 |
| M | L | Q | S | L | A | G | S | S | C | V | R | L | V | E | R | H | R | S | 19 |

| GCC | TGG | TGC | TTC | GGC | TTC | CTG | GTG | CTG | GGC | TAC | TTG | CTC | TAC | CTG | GTC | TTC | GGC | GCA | 114 |
|---|---|---|---|---|---|---|---|---|---|---|---|---|---|---|---|---|---|---|---|
| A | W | C | F | G | F | L | V | L | G | Y | L | L | Y | L | V | F | G | A | 38 |

| GTG | GTC | TTC | TCC | TCG | GTG | GAG | CTG | CCC | TAT | GAG | GAC | CTG | CTG | CGC | CAG | GAG | CTG | CGC | 171 |
|---|---|---|---|---|---|---|---|---|---|---|---|---|---|---|---|---|---|---|---|
| V | V | F | S | S | V | E | L | P | Y | E | D | L | L | R | Q | E | L | R | 57 |

| AAG | CTG | AAG | CGA | CGC | TTC | TTG | GAG | GAG | CAC | GAG | TGC | CTG | TCT | GAG | CAG | CAG | CTG | GAG | 228 |
|---|---|---|---|---|---|---|---|---|---|---|---|---|---|---|---|---|---|---|---|
| K | L | K | R | R | F | L | E | E | H | E | C | L | S | E | Q | Q | L | E | 76 |

| CAG | TTC | CTG | GGC | CGG | GTG | CTG | GAG | GCC | AGC | AAC | TAC | GGC | GTG | TCG | GTG | CTC | AGC | AAC | 285 |
|---|---|---|---|---|---|---|---|---|---|---|---|---|---|---|---|---|---|---|---|
| Q | F | L | G | R | V | L | E | A | S | N | Y | G | V | S | V | L | S | N | 95 |

| GCC | TCG | GGC | AAC | TGG | AAC | TGG | GAC | TTC | ACC | TCC | GCG | CTC | TTC | TTC | GCC | AGC | ACC | GTG | 342 |
|---|---|---|---|---|---|---|---|---|---|---|---|---|---|---|---|---|---|---|---|
| A | S | G | N | W | N | W | D | F | T | S | A | L | F | F | A | S | T | V | 114 |

| CTC | TCC | ACC | ACA | GGT | TAT | GGC | CAC | ACC | GTG | CCC | TTG | TCA | GAT | GGA | GGT | AAG | GCC | TTC | 399 |
|---|---|---|---|---|---|---|---|---|---|---|---|---|---|---|---|---|---|---|---|
| L | S | T | T | G | Y | G | H | T | V | P | L | S | D | G | G | K | A | F | 133 |

| TGC | ATC | ATC | TAC | TCC | GTC | ATT | GGC | ATT | CCC | TTC | ACC | CTC | CTG | TTC | CTG | ACG | GCT | GTG | 456 |
|---|---|---|---|---|---|---|---|---|---|---|---|---|---|---|---|---|---|---|---|
| C | I | I | Y | S | V | I | G | I | P | F | T | L | L | F | L | T | A | V | 152 |

| GTC | CAG | CGC | ATC | ACC | GTG | CAC | GTC | ACC | CGC | AGG | CCG | GTC | CTC | TAC | TTC | CAC | ATC | CGC | 513 |
|---|---|---|---|---|---|---|---|---|---|---|---|---|---|---|---|---|---|---|---|
| V | Q | R | I | T | V | H | V | T | R | R | P | V | L | Y | F | H | I | R | 171 |

| TGG | GGC | TTC | TCC | AAG | CAG | GTG | GTG | GCC | ATC | GTC | CAT | GCC | GTG | CTC | CTT | GGG | TTT | GTC | 570 |
|---|---|---|---|---|---|---|---|---|---|---|---|---|---|---|---|---|---|---|---|
| W | G | F | S | K | Q | V | V | A | I | V | H | A | V | L | L | G | F | V | 190 |

| ACT | GTG | TCC | TGC | TTC | TTC | TTC | ATC | CCG | GCC | GCT | GTC | TTC | TCA | GTC | CTG | GAG | GAT | GAC | 627 |
|---|---|---|---|---|---|---|---|---|---|---|---|---|---|---|---|---|---|---|---|
| T | V | S | C | F | F | F | I | P | A | A | V | F | S | V | L | E | D | D | 209 |

FIG. 1B-1

```
TGG AAC TTC CTG GAA TCC TTT TAT TTT TGT TTT ATT TCC CTG AGC ACC ATT GGC CTG    684
 W   N   F   L   E   S   F   Y   F   C   F   I   S   L   S   T   I   G   L    228

GGG GAT TAT GTG CCT GGG GAA GGC TAC AAT CAA AAA TTC AGA GAG CTC TAT AAG ATT    741
 G   D   Y   V   P   G   E   G   Y   N   Q   K   F   R   E   L   Y   K   I    247

GGG ATC ACG TGT TAC CTG CTA CTT GGC CTT ATT GCC ATG TTG GTA GTT CTG GAA ACC    798
 G   I   T   C   Y   L   L   L   G   L   I   A   M   L   V   V   L   E   T    266

TTC TGT GAA CTC CAT GAG CTG AAA AAA TTC AGA AAA ATG TTC TAT GTG AAG AAG GAC    855
 F   C   E   L   H   E   L   K   K   F   R   K   M   F   Y   V   K   K   D    285

AAG GAC GAG GAT CAG GTG CAC ATC ATA GAG CAT GAC CAA CTG TCC TTC TCC TCG ATC    912
 K   D   E   D   Q   V   H   I   I   E   H   D   Q   L   S   F   S   S   I    304

ACA GAC CAG GCA GCT GGC ATG AAA GAG GAC CAG AAG CAA AAT GAG CCT TTT GTG GCC    969
 T   D   Q   A   A   G   M   K   E   D   Q   K   Q   N   E   P   F   V   A    323

ACC CAG TCA TCT GCC TGC GTG GAT GGC CCT GCA AAC CAT TGA gcgtaggatttgttgcatt   1030
 T   Q   S   S   A   C   V   D   G   P   A   N   H   *                        337
atgctagagcaccagggtcagggtgcaaggaagaggcttaagtatgttcatttttatcagaatgcaaaagcgaaaa  1106
ttatgtcactttaagaaatagctactgtttgcaatgtcttattaaaaaacaacaaaaaaagacacatggaacaaag  1182
aagctgtgaccccagcaggatgtctaatatgtgaggaaatgagatgtccacctaaaattcatatgtgacaaaatta  1258
tctcgaccttacataggaggagaatacttgaagcagtatgctgctgtggttagaagcagatttttatacttttaact  1334
ggaaactttggggtttgcatttagatcatttagctgatggctaaatagcaaaatttatatttagaagcaaaaaaaa  1410
aaagcatagagatgtgttttataaataggtttatgtgtactggtttgcatgtacccacccaaaatgattattttg   1486
gagaatctaagtcaaactcactatttataatgcataggtaaccattaactatgtacatataaagtataaatatgtt  1562
tatattctgtacatatggtttaggtcaccagatcctagtgtagttctgaaactaagactatagatattttgtttct  1638
tttgatttctctttatactaaagaatccagagttgctacaataaaataaggggaataataaaaaaaaaaaaaaaa   1712
```

FIG. 1B-2

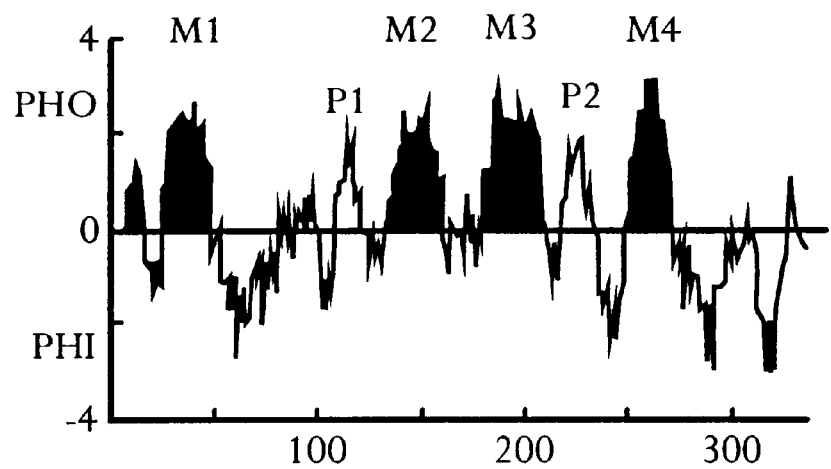
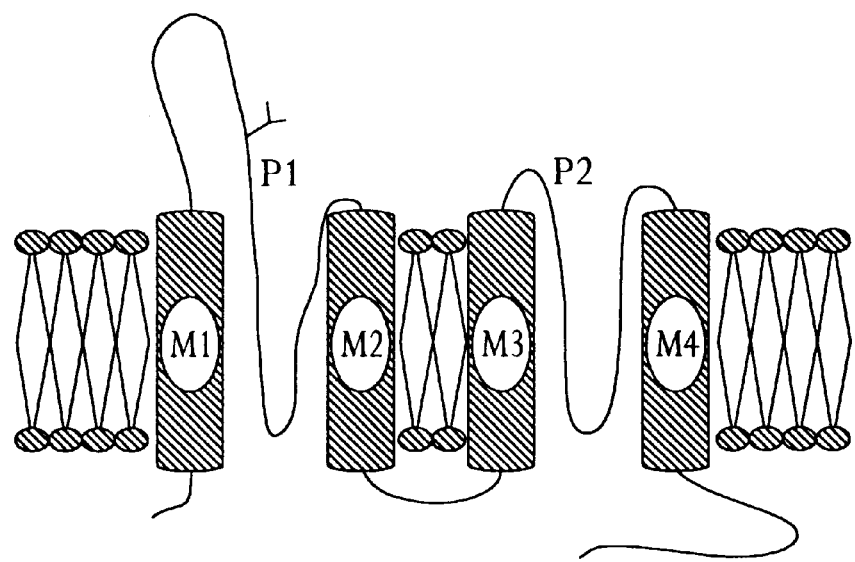
FIG. 1C

```
                    1              14                27
TWIK-1 P1   FTSALFFASTVLSTTGYGHTVPLSDGG
TWIK-1 P2   FLESFYFCFISLSTIGLGDYVPGEGYN
TOK1 P2     YFNCIYFCFLCLLTIGYGDYAPRTGAG
TOK1 P1     YGNALYFCTVSLLTVGLGDILPKSVGA
Slo         YWTCVYFLIVTMSTVGYGDVYCETVLG
Shaker      IPDAFWWAVVTMTTVGYGDMTPVGFWG
Shab        IPEAFWWAGITMTTVGYGDICPTTALG
Shal        IPAAFWYTIVTMTTLGYGDMVPETIAG
Shaw        IPLGLWWALVTMTTVGYGDMAPKTYIG
KAT1        YVTALYWSITTLTTTGYGDFHAENPRE
AKT1        YVTSMYWSITTLTTVGYGDIHPVNTKE
eag         YVTALYFTMTCMTSVGFGNVAAETDNE
ROMK1       MTSAFLFSLETQVTIGYGFRFVTEQCA
IRK1        FTAAFLFSIETQTTIGYGFRCVTDECP
GIRK1       FPSAFLFFIETEATIGYGYRYITDKCP
```

FIG. 2A

```
TWIK-1    1   MLQSLAGSSCVRLVE------RHRSAWCF--GE----------LVLGY
f17c8     1   MYTDEGEYSGDTDHGGSEMQKMSPNTRQNFRQNVNVVVCLSAAITL--
M110-2    1   MTVSMEENSKIQMLSATSKDKKVATDRSLLNKYHLGPLALHTGLVLSC

TWIK-1    31  LLYLVFGAVVFSSVELPYEDLLRQE----LRKLKRRFLEEHEC---L
f17c8     47  LVFNLIGAGIF----------------------YLAETQNSSES
M110-2    49  VIYALGGAYLFLSIEHP-EELKRREKAIREFQDLKQQFMGNITSGIEN

TWIK-1    71  SEQQLEQFLGRVL------EASNYGVSVLSNASGNWNW--DFTSALF
f17c8     69  LNENSEV--SKCLHNLPIGGKITAEMKSKLGKCLTKSSRIDGFGKAIF
M110-2    96  SEQSFEIYTKKLILMLEDAHNAHAFEYFFLNEEIPKDMW--TFSSALV

P1
TWIK-1    110 FASTVLSTTGYGHTVPLSDGGKAFCII-YSVIGIPFTLLFLTAVVQRI
f17c8     115 FSWTLYSTVGYGSLYPHSTLGRYLTIF-YSLLMIPVFIAFKFEFGTFL
M110-2    142 FLITTVIPVGYGYLFPVSAYGR-MCLIAYALLGIPLTLVTMADTGKFA

TWIK-1    157 TVH---VTRRPVL----YLHIRWGFSKQVVAIVHAVLLGFVTVSCFF
f17c8     162 AHFLVVVSNRTRLAVKKAYKLS-QNPENAETPSNSLQHDYLIFLSSI N
M110-2    189 AQL---VTR-------------W-FGDNNMAIPAAIFV-----CLL

P2
TWIK-1    197 FI-PAAVFS---VL--EDDWNFLESFYFCFISLSTIGLGDYVPGEGYN
f17c8     209 LLCSEGLLSSSAFFSSIENISYLSSVYFGITMFLIGIGDIVPTN---
M110-2    213 FAYPLVVGF---LLCSTSNITYLDSVYFSLTSIFTIGFGDLTP-----

TWIK-1    239 QKFRELYKIGIECYLELGLIAMLVVDETFC----ELHELKKER-----
f17c8     254 -------LVWFSGYCMLFLISDVLSNQIFYFCQARVRYFFHILARKIL
M110-2    253 ----DMNVIHMVLFLAVGVILVTITLDIVA---AEMIDRVHYMGRHYG

TWIK-1    278 -------KMFYVKKDKDEDQVHIIEHDQL----SESSITDQAAGMKED
f17c8     295 LLRE-EDDGFQLETTVSLQHIPILNSQCMPSL----VLDCEKEELDND
M110-2    294 KAKELAGKMFQLAQSLNMKQGLVSGVGQLHALARFGMLVGREEVDKTQ

TWIK-1    315 QKQNEPFVAT---------------QSSACVDGPANH----
f17c8     338 EKLISSLFST-------------------------------
M110-2    342 EDGIIAFSPDVMDGLEFMDTLSIYSRRSRRSAENSARNLFLS
```

FIG. 2B

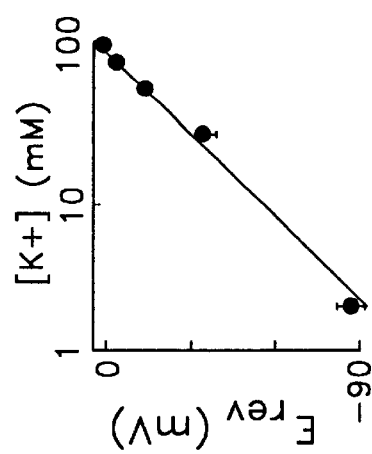
FIG. 3C
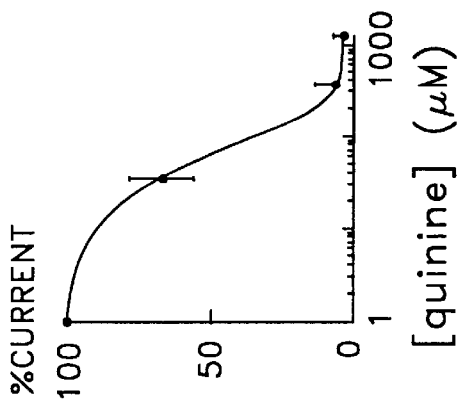
FIG. 3F
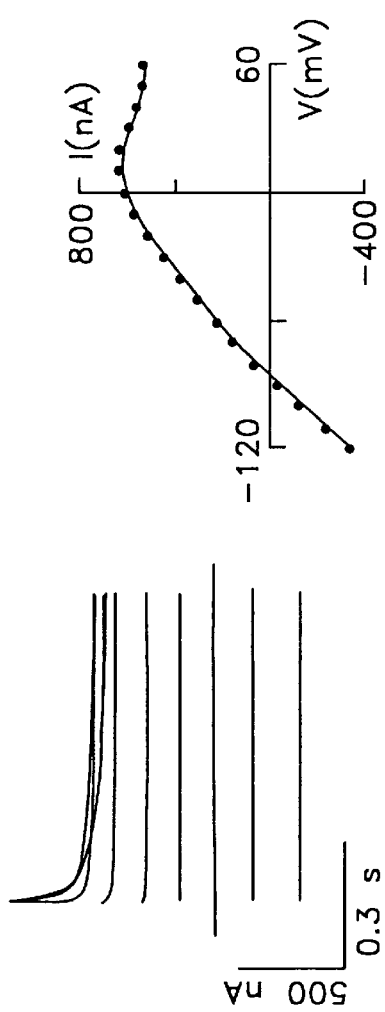
FIG. 3B
FIG. 3E
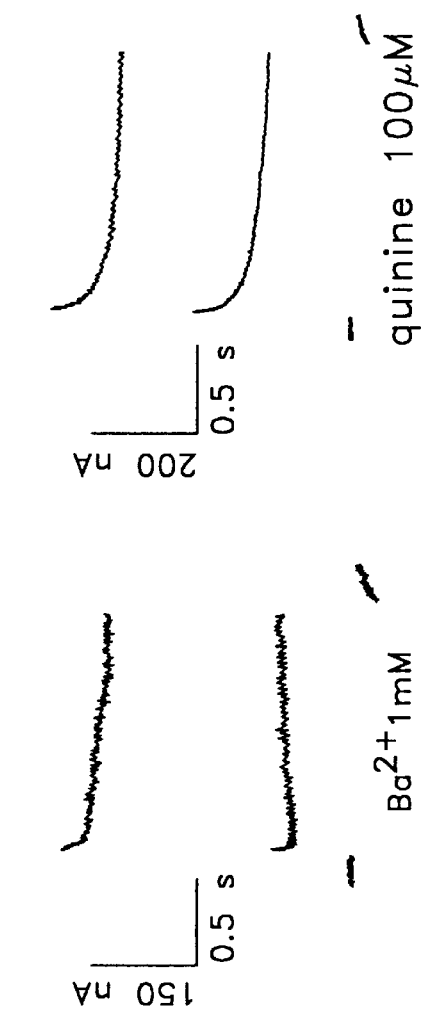
FIG. 3A
FIG. 3D

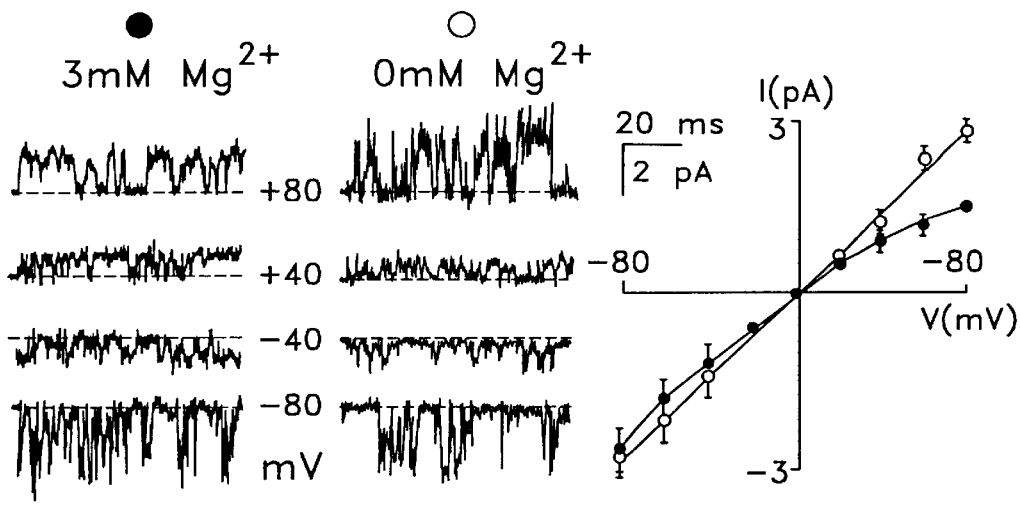
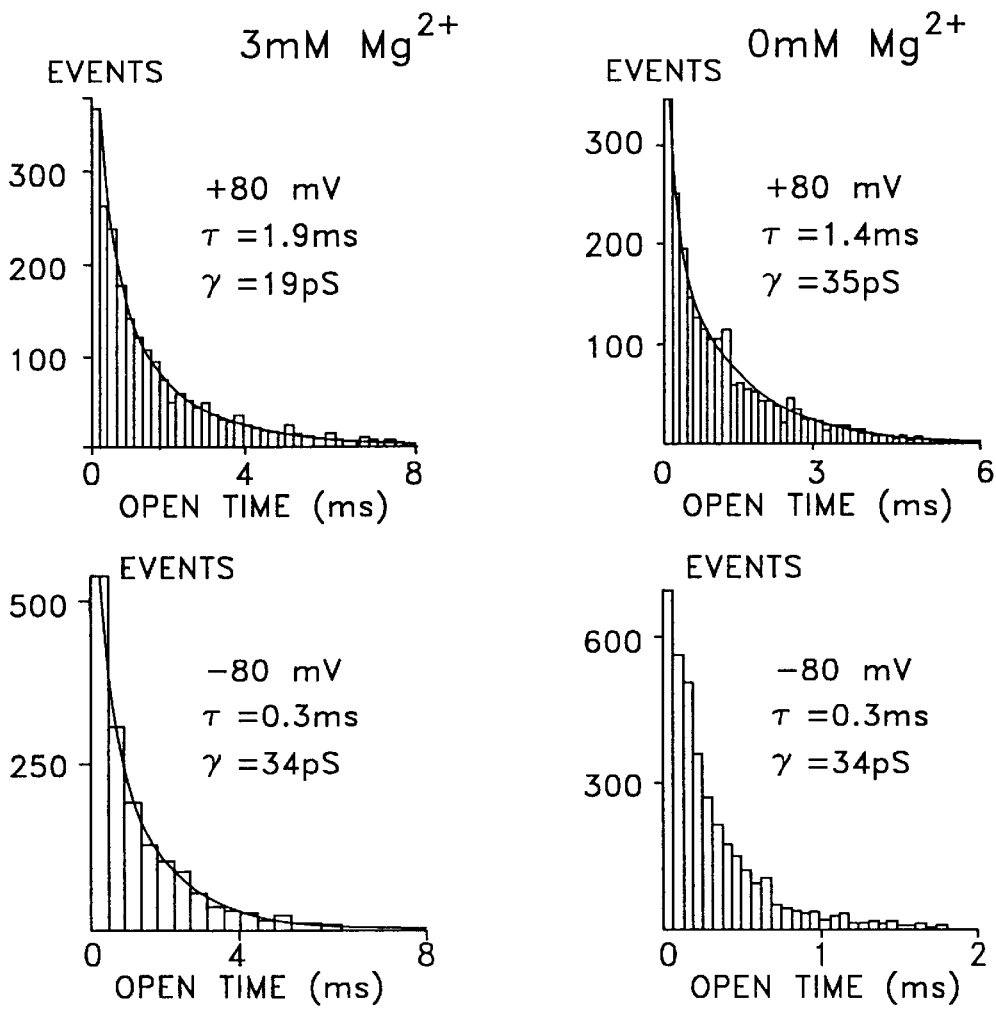
FIG. 5A    FIG. 5B
FIG. 5C    FIG. 5D

```
                                         tgccctgcgcggatagcggcgagcgcagccatgccccaggccgcctccg  -77
gggcagcagcagcggcggccggggccgatgcgcgggccggggcgccggggggccggcggcggcccgggcgggacg   -1
```

| ATG | AAG | CGG | CAG | AAC | GTG | CGC | ACG | CTG | GCG | CTC | ATC | GTG | TGC | ACC | TTC | ACC | TAC | CTG | 57 |
|---|---|---|---|---|---|---|---|---|---|---|---|---|---|---|---|---|---|---|---|
| M | K | R | Q | N | V | R | T | L | A | L | I | V | C | T | F | T | Y | L | 19 |
|   |   |   | E | N | V | R | T | L | A | L | I | V | C | T | F | T | Y | L |   |

| CTG | GTG | GGC | GCC | GCG | GTC | TTc | GAC | GCG | CTG | GAG | TCG | GAG | CCC | GAG | CTG | ATC | GAG | CGG | 114 |
|---|---|---|---|---|---|---|---|---|---|---|---|---|---|---|---|---|---|---|---|
| L | V | G | A | A | V | F | D | A | L | E | S | E | P | E | L | I | E | R | 38 |
| L | V | G | A | A | V | F | D | A | L | E | S | E | P | E | M | I | E | R |   |

| CAG | CGG | CTG | GAG | CTG | CGG | CAG | CAG | GAG | CTG | CGG | GCG | CGC | TAC | AAC | CTC | AGC | CAG | GGC | 171 |
|---|---|---|---|---|---|---|---|---|---|---|---|---|---|---|---|---|---|---|---|
| Q | R | L | E | L | R | Q | Q | E | L | R | A | R | Y | N | L | S | Q | G | 57 |
| Q | R | L | E | L | R | Q | L | E | L | R | A | R | Y | N | L | S | E | G |   |
|   |   |   |   |   |   |   |   |   |   |   |   |   |   | * |   |   |   |   |   |

| GGC | TAC | GAG | GAG | CTG | GAG | CGC | GTC | GTG | CTG | CGC | CTC | AAG | CCG | CAC | AAG | GCC | GGC | GTG | 228 |
|---|---|---|---|---|---|---|---|---|---|---|---|---|---|---|---|---|---|---|---|
| G | Y | E | E | L | E | R | V | V | L | R | L | K | P | H | K | A | G | V | 76 |
| G | Y | E | E | L | E | R | V | V | L | R | L | K | P | H | K | A | G | V |   |

| CAG | TGG | CGC | TTC | GCC | GGC | TCC | TTC | TAC | TTC | GCC | ATC | ACC | GTC | ATC | ACC | ACC | ATC | GGC | 285 |
|---|---|---|---|---|---|---|---|---|---|---|---|---|---|---|---|---|---|---|---|
| Q | W | R | F | A | G | S | F | Y | F | A | I | T | V | I | T | T | I | G | 95 |
| Q | W | R | F | A | G | S | F | Y | F | A | I | T | V | I | T | T | I | G |   |

| TAC | GGG | CAC | GCG | GCA | CCC | AGC | ACG | GAT | GGC | GGC | AAG | GTG | TTC | TGC | ATG | TTC | TAC | GCG | 342 |
|---|---|---|---|---|---|---|---|---|---|---|---|---|---|---|---|---|---|---|---|
| Y | G | H | A | A | P | S | T | D | G | G | K | V | F | C | M | F | Y | A | 114 |
| Y | G | H | A | A | P | S | T | D | G | G | K | V | F | C | M | F | Y | A |   |

| CTG | CTG | GGC | ATC | CCG | CTC | ACG | CTC | GTC | ATG | TTC | CAG | AGC | CTG | GGC | GAG | CGC | ATC | AAC | 399 |
|---|---|---|---|---|---|---|---|---|---|---|---|---|---|---|---|---|---|---|---|
| L | L | G | I | P | L | T | L | V | M | F | Q | S | L | G | E | R | I | N | 133 |
| L | L | G | I | P | L | T | L | I | M | F | Q | S | L | G | E | R | I | N |   |

| ACC | TTG | GTG | AGG | TAC | CTG | CTG | CAC | CGC | GCC | AAG | AAG | GGG | CTG | GGC | ATG | CGG | CGC | GCC | 456 |
|---|---|---|---|---|---|---|---|---|---|---|---|---|---|---|---|---|---|---|---|
| T | L | V | R | Y | L | L | H | R | A | K | K | G | L | G | M | R | R | A | 152 |
| T | F | V | R | Y | L | L | H | R | A | K | R | G | L | G | M | R | H | A |   |

| GAC | GTG | TCC | ATG | GCC | AAC | ATG | GTG | CTC | ATC | GGC | TTC | TTC | TCG | TGC | ATC | AGC | ACG | CTG | 513 |
|---|---|---|---|---|---|---|---|---|---|---|---|---|---|---|---|---|---|---|---|
| D | V | S | M | A | N | M | V | L | I | G | F | F | S | C | I | S | T | L | 171 |
| E | V | S | M | A | N | M | V | L | I | G | F | V | S | C | I | S | T | L |   |

| TGC | ATC | GGC | GCC | GCC | GCC | TTC | TCC | CAC | TAC | GAG | CAC | TGG | ACC | TTC | TTC | CAG | GCC | TAC | 570 |
|---|---|---|---|---|---|---|---|---|---|---|---|---|---|---|---|---|---|---|---|
| C | I | G | A | A | A | F | S | H | Y | E | H | W | T | F | F | Q | A | Y | 190 |
| C | I | G | A | A | A | F | S | Y | Y | E | R | W | T | F | F | Q | A | Y |   |

| TAC | TAC | TGC | TTC | ATC | ACC | CTC | ACC | ACC | ATC | GGC | TTC | GGC | GAC | TAC | GTG | GCG | CTG | CAG | 627 |
|---|---|---|---|---|---|---|---|---|---|---|---|---|---|---|---|---|---|---|---|
| Y | Y | C | F | I | T | L | T | T | I | G | F | G | D | Y | V | A | L | Q | 209 |
| Y | Y | C | F | I | T | L | T | T | I | G | F | G | D | Y | V | A | L | Q |   |

| AAG | GAC | CAG | GCC | CTG | CAG | ACG | CAG | CCG | CAG | TAC | GTG | GCC | TTC | AGC | TTC | GTC | TAC | ATC | 684 |
|---|---|---|---|---|---|---|---|---|---|---|---|---|---|---|---|---|---|---|---|
| K | D | Q | A | L | Q | T | Q | P | Q | Y | V | A | F | S | F | V | Y | I | 228 |
| K | D | Q | A | L | Q | T | Q | P | Q | Y | V | A | F | S | F | V | Y | I |   |

| CTT | ACG | GGC | CTC | ACG | GTC | ATC | GGC | GCC | TTC | CTC | AAC | CTC | GTG | GTG | CTG | CGC | TTC | ATG | 741 |
|---|---|---|---|---|---|---|---|---|---|---|---|---|---|---|---|---|---|---|---|
| L | T | G | L | T | V | I | G | A | F | L | N | L | V | V | L | R | F | M | 247 |
| L | T | G | L | T | V | I | G | A | F | L | N | L | V | V | L | R | F | M |   |

FIG. 8A

```
ACC ATG AAC GCC GAG GAC GAG AAG CGC GAC GCC GAG CAC CGC GCG CTG CTC ACG CGC    798
 T   M   N   A   E   D   E   K   R   D   A   E   H   R   A   L   L   T   R    266
 T   M   N   A   E   D   E   K   R   D   A   E   H   R   A   L   L   T   H

AAC GGG CAG GCG GGC GGC GGC GGA GGG GGT GGC AGC GCG CAC ACT ACG GAC ACC GCC    855
 N   G   Q   A   G   G   G   G   G   G   G   S   A   H   T   T   D   T   A    285
 N   G   Q   A   V   G   L   G   G   L   S   C   L   S   G   S   L   G   D

TCA TCC ACG GCG GCA GCG GGC GGC GGC GGC TTC CGC AAC GTC TAC GCG GAG GTG CTG    912
 S   S   T   A   A   A   G   G   G   G   F   R   N   V   Y   A   E   V   L    304
VRPRDPV  TC  AA   A   A    G GVGVGVGGS  G   F   R   N   V   Y   A   E   V   L

CAC TTC CAG TCC ATG TGC TCG TGC CTG TGG TAC AAG AGC CGC GAG AAG CTG CAG TAC    969
 H   F   Q   S   M   C   S   C   L   W   Y   K   S   R   E   K   L   Q   Y    323
 H   F   Q   S   M   C   S   C   L   W   Y   K   S   R   E   K   L   Q   Y
                                                                         •

TCC ATC CCC ATG ATC ATC CCG CGG GAC CTC TCC ACG TCC GAC ACG TGC GTG GAG CAG   1026
 S   I   P   M   I   I   P   R   D   L   S   T   S   D   T   C   V   E   Q    342
 S   I   P   M   I   I   P   R   D   L   S   T   S   D   T   C   V   E   H

AGC CAC TCG TCG CCG GGA GGG GGC GGC CGC TAC AGC GAC ACG CCC TCG CGA CGC TGC   1083
 S   H   S   S   P   G   G   G   G   R   Y   S   D   T   P   S   R   R   C    361
 S   H   S   S   P   G   G   G   G   R   Y   S   D   T   P   S   H   P   C
                                                                 ■

CTG TGC AGC GGG GCG CCA CGC TCC GCC ATC AGC TCG GTG TCC ACG GGT CTG CAC AGC   1140
 L   C   S   G   A   P   R   S   A   I   S   S   V   S   T   G   L   H   S    380
 L   C   S   G   T   Q   R   S   A   I   S   S   V   S   T   G   L   H   S

CTG TCC ACC TTC CGC GGC CTC ATG AAG CGC AGG AGC TCC GTG TGA ctgccccgagggacc  1200
 L   S   T   F   R   G   L   M   K   R   R   S   S   V   *                    395
 L   A   A   F   R   G   L   M   K   R   R   S   S   V
     ■                                    ▲   ▲
tggagcacctggggcgcgggcgggggacccctgctgggaggccaggagactgcccctgctgccttctgcccagtg  1276
ggacccccgcacaacatccctcaccactctcccccagcaccccatctccgactgtgcctgcttgcaccagccggca 1352
ggaggccgggctctgaggacccctcggggagccctccctccctttgaaaatctaagaagctcccagtcctcagagacccct 1428
tcagggaggaaaggcagaagctgggagcctccctccctttgaaaatctaagaagctcccagtcctcagagaccct 1504
gctggtaccacaccccaccttcggaggggacttcatgttccgtgtacgtttgcatctctattttatacctctgtcct 1580
gctaggtctccaccttcccttggttccaaaagccagggtgtctatgtccaagtcaccctactcagcccactcc   1656
ccttcctcatccccagctgtgtctcccaacctcccttcgtgttgttttgcatggctttgcagttatggagaaagtg 1732
gaaaccagcagtccctaaagctggtccccagaaagcaggacagaaagaaggagggacaggcaggcagcaggaggg 1808
gcgagctgggaggcaggaggcagcggcctgtcagtctgcagaatggtcgcactggaggttcaagctaactggcctc 1884
cagccacattctcatagcaggtaggacttcagccttccagacactgcccttagaatctggaacagaagacttcaga 1960
ctcaccataattgctgataattacccactcttaaatttgtcgagtgattttttagcctctgaaaactctatgctggc 2036
cactgattcctttgagtctcacaaaaccctacttaggtcatcagggcaggagttctcactcccattttacagatga 2112
gaatactgaggcctggacaggtgaagtgaccagagagcaaaaggcaaaggggtgggggctgggtgcagtggctcac 2188
acctgtattcccaacacttttggaggctgaggttggaggattgcttgagcccaggaattcgagaccagcctaggtg 2264
acatagtgagacccatctctacaaaaaataaaaaattaaccaggtgtggtggcacgtgcctgggagtcccagcga 2340
cttgggaggctgaggtgggaggattgtttgagcctggaggtcgaggctgtagtgagccctgattgcaccactgta 2416
ctccagcctgggtgacagggcaagaccctgtctcaaaaaaaaaaaaaa                            2465
```

FIG. 8B

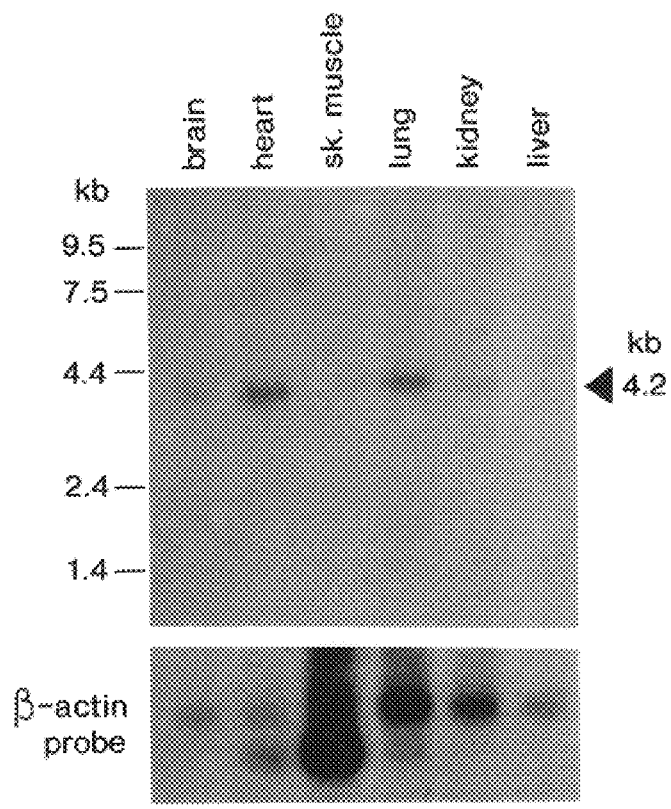
FIG. 11A
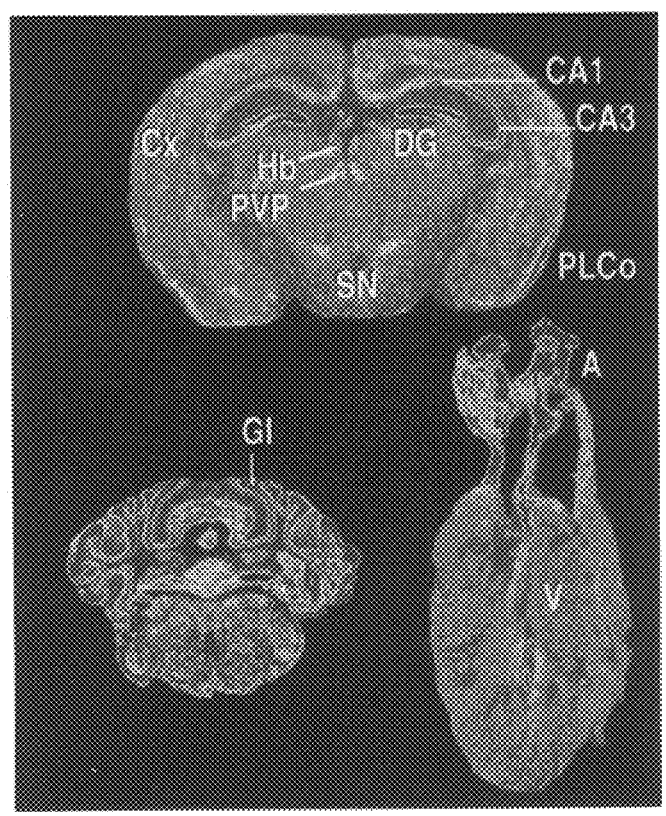
FIG. 11B
FIG. 11C
FIG. 11D

FAMILY OF MAMMALIAN POTASSIUM CHANNELS, THEIR CLONING AND THEIR USE, ESPECIALLY FOR THE SCREENING OF DRUGS

RELATED APPLICATIONS

This patent application is a continuation-in-part (CIP) of pending application Ser. No. 08/749,816 Lesage et al., filed in the U.S. on Nov. 15, 1996, now U.S. Pat. No. 6,013,476 entitled, "New Family of Mammalian Potassium Channels, Their Cloning And Their Use, Especially For The Screening of Drugs" which is incorporated herein by reference in its entirety, which claims the priority filing date of French patent application Ser. No. 96/01565, filed Feb. 8, 1996.

This application also claims the priority of provisional patent application Ser. No. 60/095,234, filed on Aug. 4, 1998, entitled "Task, a Human Background K+channel to Sense External PH Variations near Physiological PH" which is also incorporated herein by reference in its entirety.

BACKGROUND OF THE INVENTION

1. Field of Invention

The present invention relates to a new family of potassium channels. More specifically, the invention relates to the cloning of new human potassium channels that constitute the members of a new functional and structural group of potassium channels. The abundance of these channels and their presence in a large number of tissues are such as to confer on them a fundamental role in the transport of potassium in a large number of types of cells. The properties of the channels suggest highly interesting applications in the physiology of mammals, especially humans.

2. Description of the Related Art

Potassium channels are ubiquitous membrane proteins that form the largest family of ion channels both in term of functions and structures. By determining and modulating the membrane potential, they play a major role in neuronal integration, muscular excitability as well as hormone secretion (Rudy, 1988; Hille, 1992). More than 40 genes encoding $K^+$ channel subunits are now identified in mammals. These subunits fall into two structural classes of pore-forming subunits (Shaker and IRK) (Pongs, 1992; Jan and Jan, 1994; Doupnik et al., 1995; Fakler and Ruppersberg, 1996; Kohler et al., 1996) and four structural classes of auxiliary subunits (Kvβ, Kcaβ, SUR and IsK) (Takumi et al., 1988; Knaus et al., 1994; Pongs, 1995; Inagaki et al., 1996). All Shaker-type subunits have a conserved hydrophobic core containing 6 transmembrane segments (TMS). Associations of Shaker-type subunits with accessory subunits such as Kvβ, Kcaβ or IsK give rise to voltage-dependent $K^+$ channels (Pongs, 1995; Barhanin et al., 1996; Fink et al., 1996a; Sanguinetti et al., 1996) and $Ca^{2+}$-dependent $K^+$ channels (MacCobb et al., 1995; MacManus et al., 1995). Subunits of inward rectifier $K^+$ channels (IRK) have only two TMS (Doupnik et al., 1995; Lesage et al., 1995; Fakler and Ruppersberg, 1996). Some IRKs give rise to ATP-sensitive $K^+$ channels when they are associated with sulfonylurea receptors (SUR) subunits (Inagaki et al., 1996). Despite a very low overall sequence similarity, Shaker and IRK pore-forming subunits share a conserved domain called the P domain. This peculiar motif is an essential element of the $K^+$-selective filter of the aqueous pore and is considered as the signature of $K^+$ channel-forming proteins (Heginbotham et al., 1994).

In the above-identified parent patent application, there is described a new family of mammalian $K^+$ channel subunits. Despite a low sequence similarity between them (less than 28% of amino acid identity), both cloned members of that family (TWIK-1 and TREK-1) possess the same overall structure with four TMS and two P domains (Fink et al., 1996b; Lesage et al., 1996a; Lesage et al., 1997). The conservation of this structure is not associated with a conservation of the functional properties: TWIK-1 gives rise to weakly inward rectifier $K^+$ currents (Lesage et al., 1996a) while TREK-1 produces outward rectifier $K^+$ currents (Fink et al., 1996b). However, both channels are open at the resting potential and are able to drive the resting membrane potential near the $K^+$ equilibrium potential. This common property suggests that these channels control the resting membrane potential in a large set of cell types.

BRIEF DESCRIPTION OF THE INVENTION

The present invention describes the cloning, the tissue distribution and the expression of a novel human member of this new structural family. This channel, called TASK for TWIK-related Acid-Sensitive $K^+$ channel, as far as is known to the inventors is the first cloned mammalian channel that produces $K^+$ currents that possess all the characteristics of background conductances. They are instantaneous with voltage changes and their current-voltage relationships fits the curves predicted from the constant field theory for simple electrodiffusion through an open $K^+$-selective pore indicating that TASK currents are voltage-insensitive. The activity of this background channel is strongly dependent on the external pH in the physiological range suggesting that this particular channel is a sensor of external pH variations.

The discovery of this new member of potassium channels and the cloning of the new member of this family provides, notably, new means for screening drugs capable of modulating the activity of these new potassium channels, and thus of preventing or treating the diseases in which these channels are involved.

BRIEF DESCRIPTION OF NUCLEOTIDE AND AMINO ACID SEQUENCES

The research activities that led to the cloning of the TWIK-1 and TASK channels was carried out in the manner described below with reference to the attached sequences and figures in which:

SEQ ID NO:1 represents the nucleotide sequence of the CDNA of TWIK1 and its deduced amino acid sequence.

SEQ ID NO:2 represents the amino acid sequence of the TWIK-1 protein.

SEQ ID NO:3 represents the nucleotide sequence of the CDNA of TASK and its deduced amino acid sequence.

SEQ ID NO:4 represents the amino acid sequence of the TASK protein.

DESCRIPTION OF THE FIGURES

FIGS. 2(a–b) represents the sequence alignments. (a): alignment of the P domains of TWIK-1, TOC/YORK and other representative K+channel families (SEQ ID NO:9 THROUGH SEQ ID NO:23); the identical and conserved residues are circled in black and in gray, respectively. (b): alignment of TWIK-1 (SEQ ID NO:2) with potential homologs of; the sequences M110.2 (SEQ ID NO:7) and F17C8.5 (SEQ ID NO:2) were deduced from the gene sequences (respective access numbers Z49968 and Z35719); the computerized splicing of the other genornic sequences of C. elegans (respective access numbers Z49889, P34411 and Z22180) is not sufficiently precise to allow their perfect alignment and is therefore not shown.

FIGS. 3(a–f) shows the biophysical and pharmacological properties of K+ currents recorded by the imposed voltage technique on Xenopus oocytes that had received an injection of TWIK-1 cRNA; (a): the oocyte was maintained at a holding potential (HP) of –80 mV and the currents were recorded at the end of 1-s voltage jumps from –120 to +60 mV in 20 mV increments. (b): regular current-voltage relationship using the same technique as in (a). (c): potential reversal of the TWIK-1 currents ($E_{rev}$) as a function of the external K+ concentration. (d) current tracings linked to +30 mV depolarizations starting at a holding potential (HP) of –80 mV in the absence (top tracing) and in the presence (bottom tracing) of 1 mM of $Ba^{2+}$. (e): blocking effect of 100 $\mu$M of quinine, same protocol as in (d). (f) dose-response relationship of the blocking of the TWIK-1 currents by quinine.

FIGS. 5(a–d) shows the properties of the single TWIK-1 channel. (a): current tracings recording in the input-output configuration to the membrane potentials indicated in the absence (m) or in the presence (.) of internal $M^{2+}$ (3 mM) and in symmetry with 140 mM of K+. (b): mean of curves I–V (n=10). (c and d): open time of distribution obtained at +80 mV (top histograms) and at –80 mV (bottom histograms) in the presence of 3 mM $Mg^{2+}$ (c) or in the absence of $Mg^{2+}$ (d).

FIG. 8 (which consists of 8A and 8B, an enlargement of 8A) show the nucleotide and deduced amino acid sequences of human TASK (SEQ ID NO:3) and partial amino acid sequence of mouse TASK (SEQ ID NO:5). Consensus sites for N-linked glycosylation (*) and phosphorylation by protein kinase C (n), protein kinase A (s) and tyrosine kinase (l) in human TASK. These sites have been identified by using the prosite server (European Bioinformatics Institute) with the ppsearch software (EMBL Data library) based on the MacPattern program. The sequence of human and mouse TASK have been deposited in the GenBank/EMBL database under the accession numbers AF006823 and AF006824, respectively.

FIGS. 11(A–B) shows the distribution of TASK mRNA in adult mouse. A: Northern blot analysis. Each lane contains 2 $\mu$g of poly(A)+RNA. Autoradiograms were exposed for 72 h at –70° C. The blots were re-probed with a $\beta$-actin cDNA probe for control. B, C, D:In situ hybridization analysis from a coronal section at the level of the forebrain (B), the cerebellum (C), and the heart (D). Warmer colors represent higher levels of expression. CA1–CA3: fields CA1–3 of Ammon's horn, Cx: cerebral cortex, DG: dentate gyrus, Gl: granular layer, Hb: habenula, SN: substantia nigra, PLCo: postero lateral cortical amygdaloid nuclei, PVP: paraventricular thalamic nucleus, A: atrium, V: ventricule.

$$I_{K^+} = P_{K^+} \left( \frac{[K^+]_{out}}{K_{0.5} + [K^+]_{out}} \right) \left( \frac{V_m F^2}{RT} \right) \frac{[K^+]_{in} - [K^+]_{out} e^{-VF/RT}}{1 - e^{-VF/RT}}$$

where $I_{K^+}$ is the potassium current, $P_{K^+}$ is the apparent permeability for K$^+$, $K_{0.5}$ the half maximum activation by K$^+$, $[K^+]_{out}$ and $[^+]_{in}$ are the external and internal K$^+$ concentrations, $V_m$ the membrane potential, F, R and T have their usual meanings. The classical GHK relation has been modified with:

$$\frac{[K^+]_{out}}{K_{0.5} + [K^+]_{out}}$$

to take into account the sensitivity of the conductance to external K$^+$. E: TASK currents recorded from a transfected COS cell and elicited by voltage pulses from −150 mV to +50 mV in 40 mV steps, 500 ms in duration, from a holding potential of −80 mV, in low (5 mM K$^+$) or high K$^+$ solutions (155 mM K$^+$). The zero current level is indicated by an arrow. F: Current-voltage relationships. Mean currents were measured over the last 50 ms at the end of voltage pulses ranging from −150 to +50 mV in 10 mV steps as in E. Solutions containing 5 mM K$^+$ and 150 mM TMA were used, TMA was then substituted by K$^+$ to obtain solutions ranging from 5 mM to 155 mM K$^+$.

FIGS. 13(A–D) shows the pH dependent regulation of TASK in Xenopus oocytes and COS cells. A: Current-voltage relationships recorded from a TASK-expressing oocyte with a ramp ranging from −150 mV to +50 mV, 500 ms in duration, from a holding potential of −80 mV, in ND96 solution at pH 6.5, 7.4 or 8.4. Inset: Currents elicited by voltage pulses to +50 mV, 500 ms in duration, in the same conditions as above. The zero current level is indicated by an arrow. B: pH-dependence of TASK activity in Xenopus oocyte recorded at −50, 0 and +50 mV (mean±SEM, n=3) as in A. Data were fitted with a Boltzman relation. C: Current-voltage relation recorded from a TASK-expressing COS cell with a ramp ranging from −150 mV to +50 mV, 500 ms in duration, from a holding potential of −80 mV, in 5 mM K$^+$ solution at pH 6.1, 7.4 and 8.4. Inset: Currents elicited by voltage pulses to +50 mV, 500 ms in duration, in the same conditions as above. The zero current level is indicated by an arrow. D: pH-dependence of TASK activity recorded in COS cell at −50, 0 and +50 mV (mean±SEM, n=3) as in C. Data were fitted with a Boltzman relationship.

CLONING AND PRIMARY STRUCTURE OF TWIK-1.

Figure 1A:
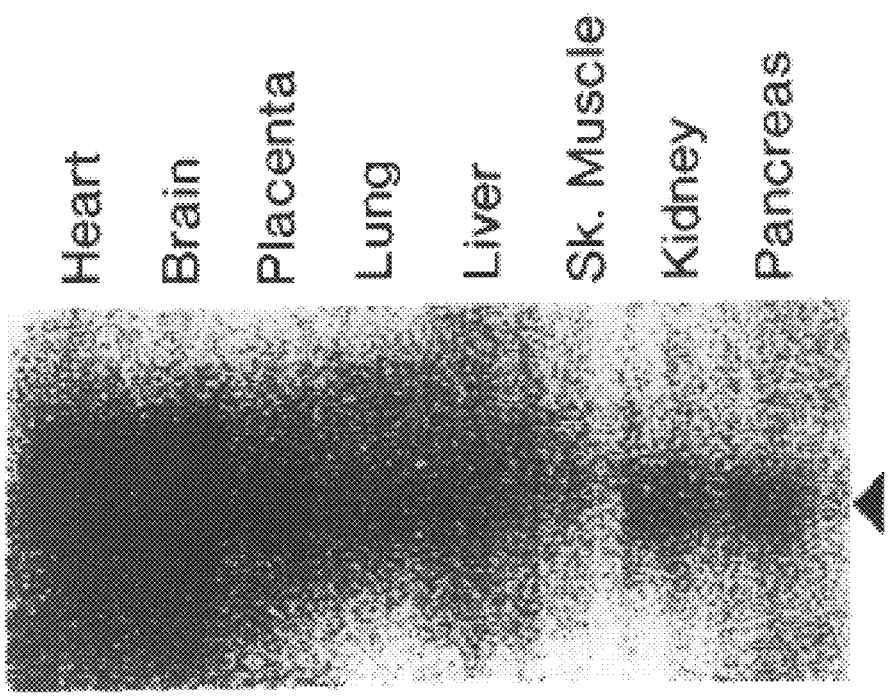
FIGS. 1(a–c) represents the Northern blot analysis, the nucleotide sequences and the deduced amino acid sequence, as well as the hydrophobicity profile of TWIK-1 (SEQ ID NO:1). (a): expression of TWIK-1 mRNA in human tissues; each track contains 5 µg of poly(A)+RNA; the autoradiograph was exposed for 24 hours. (b) cDNA sequence of TWIK-1 and the amino acid sequences of the coding sequence. The supposed transmembranal segments are circled and the P domains are underlined; □ represents a potential glycosylation site and ■ represents the threonine residue in the consensus recognition site of protein kinase C. (c): the hydrophobicity analysis and the topology of TWIK-1 deduced from it; the hydrophobicity values were calculated according to the method of Kyte and Doolittle (window size of 11 amino acids) and are presented in relation to the position of the amino acid; the shaded hydrophobic peaks correspond to the transmembranal segments.

The P domains of K+channels were used to determine the corresponding sequences in the GenBank data base by means of the BLAST sequence alignment program (Altschul, S. F. et al., 1990, J. Mol. Biol., 215, 403–410). There was thus identified a 298 bp human Tag expressed sequence (EST, HSC3AH031), the deduced amino acid sequence of which includes a nonconventional "P-like" domain sequence: GLG in place of GYG as shown in FIG. 2a. It was then envisaged that this EST sequence was a partial copy of a mRNA coding a new type of K+ channel subunit. A DNA probe was prepared from this sequence in order to carry out hybridization with a Northern blot (Clontech) of multiple human tissues. A 1.9 kb transcript was thereby found in abundance, as shown in FIG. 1a, in the heart and the brain and, at lower levels, in the placenta, the lung, the liver and the kidney. The DNA probe was used to screen a bank of kidney cDNA and four independent clones were obtained. The cDNA inserts of 1.8 to 1.9 kb of these clones all have the same open reading frame (ORE) containing a region identical to the 298 bp sequence of HSC3AH031 and differing solely in the length of their noncoding 5' sequences.

The TWIK-1 coding sequence was amplified using a low-error rate DNA polymerase (Pwo DNApal, Boehringer) and subcloned in the plasmid pEXO so as to yield pEXO-TWIK-1. Mutations were performed using the whole plasmid pEXO-TWIK-1 with a highly reliable PCR extension kit (Boehringer) and two adjacent primers. One of these introduced a punctiform mutation in the IlNIK-1 coding sequence, changing the 161 Thr codon into a codon for alanine. The product of the PCR was linearized by the enzyme BamHI and the cRNA were synthesized using a T7 RNA polymerase (Stratagene). Preparation of the X. larvis oocytes and cRNA injection were carried out in accordance with the literature (Guillemare, E. et al., 1992, Biochemistry, 31, 1246312468.

Primary Structure of TWIK-1

The following characteristics of this K+ channel were demonstrated:

The sequences of the cDNA clones contain an ORE of 1011 nucleotides (SEQ ID NO:3) coding for a polypeptide of 336 amino (SEQ ID NO:2) acids shown in FIG. 1b (SEQ ID NO:1).

The protein has two P domains.

Other than the P domains, no significant alignment was seen between TWIK-1 and a K+ channel recently cloned in yeast and which also has two P domains (Ketchum, K. A. et al., 1995, Nature, 376, 690–695).

Analysis of the hydrophobicity of TWIK- 1, shown in FIG. 1c, reveals the presence of four transmembranal domains, designated T1 to T4

By placing the $NH_2$ end on the cytoplasmic surface, in accordance with the absence of signal peptide, one obtains the topology model shown in FIG. 1c.

In this model, the two P domains are inserted in the membrane from the exterior in accordance with the known orientation of these loops in the K+ channels.

In addition, the general structural unit of TWIK-1 is similar to the unit that one would obtain by making a tandem of two classical subunits rectifying the entry of a potassium channel. Like a classical inward rectifier, TWIK-1 does not exhibit the highly conserved segment S4 which is responsible for the sensitivity to the membrane potential of the inward rectification of the K+ channels of the Kv family.

An unusual large loop of 59 amino acids is present between M1 and P1, such as to extend the length of the linker M1-P1 of the extracellular side of the membrane.

A potential site of N-glycosylation is present in this loop.

Three consensus sites of phosphorylation are present at the N-terminal (Ser 19 for calcium calmodulin kinase II) and C-terminal (Ser 303 for casein kinase II) ends of the cytoplasmic domains, and in the M2-M3 linker (Thrl61 for protein kinase II).

The alignment of the P domains of an important group of $K^+$ channels is presented in FIG. 2a. It shows that the regions constituting the pore selective for $K^+$ are well conserved including the G residues in position 16 and 18 and three other residues indicating practically exclusively conservative changes in positions 7, 14 and 17. It is of interest to note that a leucine residue is present in the place of a tyrosine conserved in position 18 in the P2 domain of TWIK-1, or of a phenylalanine in position 17 of the P domain of the $K^+$ channel of type eag.

Functional expression of TWIK-1

For the functional study, the coding sequence of TWIK-1 was inserted between the noncoding sequences 5' and 3' of *Xenopus globin* in the vector pEXO (Lingueglia, E. et al., 1993, J. Biol. Chem., 269, 13736–13739). A complementary RNA (cRNA) was transcribed of this construction and injected in the oocytes of *X laevis*. In a 0.3 ml perfusion chamber, a single oocyte was impaled on two standard glass microelectrodes (0.5–2.0 MW) charged with 3 M KCl and maintained under voltage-clamp with a Dagan TEV200 amplifier. The bath solution contained 98 mM KCl, 1.8 mM $CaCl_2$, 2 mM $MgCl_2$ and 5 mM HEPES at pH 7.4 with KOH. Stimulation of the preparation, data acquisition and analyses were carried out with the pClamp program (Axon Instruments) USA3.

For the patch-clamp experiments, the vitelline membrane was removed from the oocytes as described in the literature (Duprat, F. et al., 1995, Biochem. Biophys. Res. Commun., 212, 657–663); the oocytes were then placed in a bath solution containing 140 mM KCl, 1.8 mM $CaCl_2$, 2 mM $MgCl_2$ and 5 mM HEPES at pH 7.4 with KOH. The pipettes were filled with a strong $K^+$ solution (40 mM KCl, 100 mM of potassium methane sulfonate, 1.8 mM $CaCl_2$, 2 m M $MgCl_2$ and 5 mM HEPES adjusted to pH 7.4 with KOH). 100 $\mu$M of $GdCl_3$ was added to the pipette solution to inhibit the action of the activated channel. The inside-out patches were perfused with a solution containing 140 mM KCl, 10 mM $CaCl_2$, 5 mM HEPES adjusted to pH 7.2 with KOH and 5 m M EGTA added daily. The single channel signals were filtered at 3.5 kHz and analyzed with the Biopatch program (Big-Logic, Grenoble, France).

A noninactivating current, free from noninjected cells, was measured by the imposed voltage technique, as shown in FIG. 3a. Kinetic activation of the current is usually instantaneous and cannot be resolved because it is masked by the capacitive discharge of the current recorded at the beginning of the impulse. The current-voltage relationship is linear above 0 mV and then saturates for a stronger depolarization of the membrane, as shown in FIG. 3b. TWIK-1 is therefore $K^+$ selective. In the case of a replacement of the external $K^+$ by Na+ or N-methyl-D-gluconate, the reversal of the potential of the currents follows the $K^+$ equilibrium potential (EK), as shown in FIG. 3c. In addition, a change by 10 in the concentration [(K)]o leads to a change of 56 +/–2 mV in the inversion value of the potential, in accordance with Nernst's equation.

As shown in FIG. 3, the $K^+$ currents of TWIK-1 are inhibited by $Ba^{2+}$ (FIG. 3d) with an $IC_{50}$ value of 100 $\mu$M, by quinine (FIGS. 3e and 3f) and by quinidine (not shown) with respective $IC_{50}$ values of 50 and 95 $\mu$M. The TWIK-1 currents are slightly sensitive to TEA and to the class III antiarrhythmic agent tedisamil (30% inhibition for each, at 20 mM and 100 $\mu$M, respectively). Less than 10% inhibition was seen after application of 4-aminopyridine (1 mM), apamin (0.3 $\mu$M), charybdotoxine (3 nM), dedrotoxine (0.1 $\mu$M), clofilium (30 $\mu$M), amiodarone (100 $\mu$M) and glibenclarnide (30 $\mu$M). The TWIK-1 channel is not sensitive to the Kit channel openers cromakaline (100 $\mu$M) and pinacidil (100 $\mu$M)

Figure 4A:
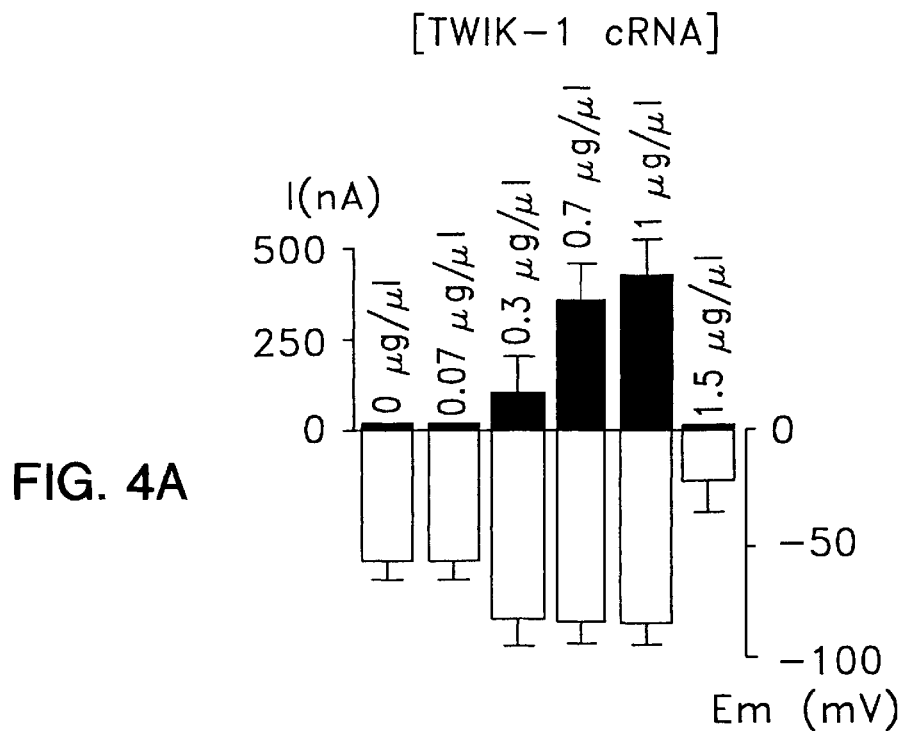
FIGS. 4(a–c) shows the influence of the expression of TWIK-1 on the membrane potential. (a): dose-response relationships of the cRNA; top row=equilibrium state of the outward currents measured at +30 mV; bottom row= membrane potentials associated with the resting state. (b): effect of 100 $\mu$M of quinine on the membrane potential of an oocyte which did not receive an injection (left tracing) and that of an oocyte that received 20 ng of TWIK-1 cRNA. (c): statistical evaluation of the depolarizing effects of 100 $\mu$M of quinine on oocytes that did not receive injections (left bars) and on oocytes that received injections of 20 ng of TWIK-1 cRNA (right bars); control (unfilled bar), +quinine (solid bars); each bar represents the mean +/– SD of 5 oocytes.
Figure 4B:
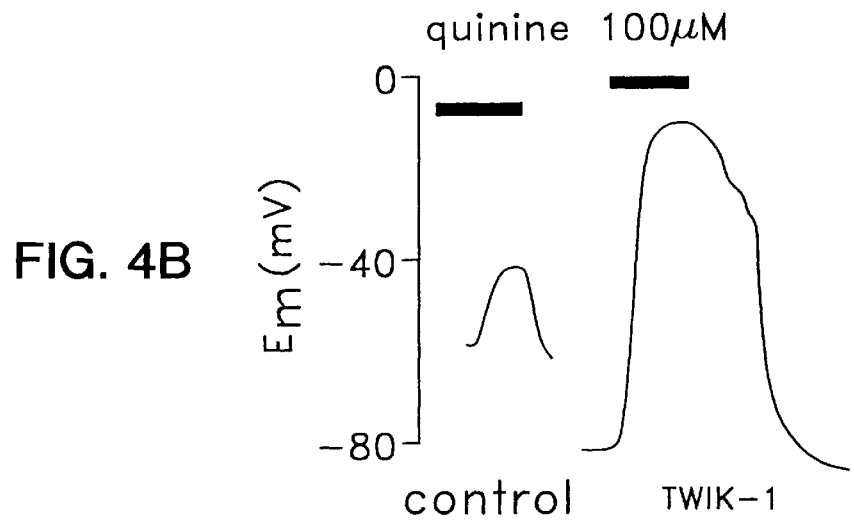
Figure 4C:
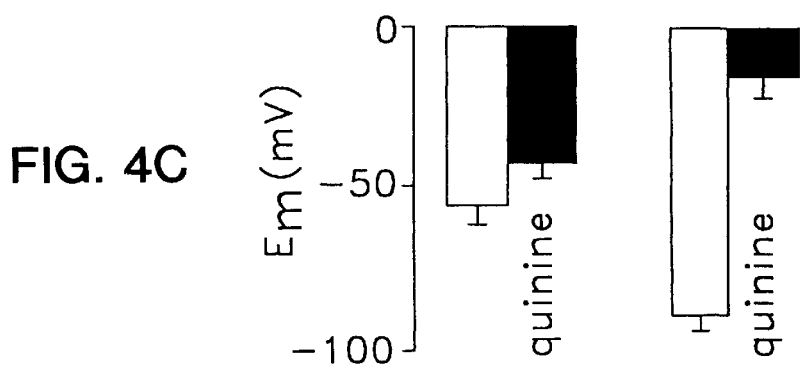

FIG. 4 shows the effect of increasing the doses of injected TWIK-1 cRNA on the independent expression of the time of the $K^+$ currents and on the resting state of the membrane potential ($E_m$). As soon as the current appears, the oocytes become increasingly polarized, reaching a value of $E_m$ close to $E_K$. The amplitude of the TWIK-1 current reaches values of 0.6 to 0.8 $\mu$M with the injection of 20 ng per oocyte. Higher doses of TWIK-1 cRNA are toxic, leading to a reduction in expression. In oocytes that received 20 ng of cRNA, quinine is the best blocker of TWIK-1, inducing a noteworthy reversible depolarization (73+/–6 mV, n=5) as shown in FIGS. 4b and 4c.

The Unitary Properties of the TWIK-1 Channel

Single channel current recordings, shown in FIG. 5, in an inside-out patch configuration or in a whole cell configuration show that the TWIK-1 channels assure the passage of influx or exit currents as a function, respectively, of a depolarization or a hyperpolarization (FIG. 5a). The current voltage relationship of the single channel, shown in FIG. 5b, shows a barely accentuated inward rectification in the presence of 3 mM (FIG. 5) and 10 mM (not shown) of $Mg^{2+}$ on the cytoplasmic side. As shown in FIG. 5b, this rectification disappears in the absence of internal $M^{2+}$. With 3 mM of internal Me+, the mean duration of opening at +80 mV is 1.9 ms and the unitary conductance is 19+/–1 pS (FIG. 5c). At –80 mV, the channels are oscillating with a mean duration of opening of 0.3 ms, and a conductance value in creasing to 34 pS. The withdrawal of the internal $Mg^{2+}$ ions does not influence the kinetic parameters under either polarized or depolarized conditions, but the unitary conductance measured at –80 mV reaches 35+/–4 pS. This apparent increase in conductance in the single channel suggests that it is the extremely rapid oscillation induced by $Mg^{2+}$ that results in an underestimation of the real value of conductance. The same properties were observed in the fixed cell configuration, showing that the channel behavior is not modified by the excision of the patch. The TWIK-1 channels in the excised patches do not discharge and do not appear to be deficient in intracellular constituents. In contrast to numerous channels which require the presence of ATP for their activity in the excised patch configuration, ATP is not required for the expression of TWIK-1. In addition, perfusion of the patch with a solution containing 10 mM of ATP does not induce any effect on the activity of the TWIK-1 channel.

Regulation of the TWIK-1 Channel

The intracellular pH ($pH_i$) is involved in the control of numerous cellular processes, and in cells such as the hepatic cells, the change in $pH_i$ regulates the membrane potential (Bear, C. E. et al., 1988, Biochim. Biophys. Acta, 944, 113–120).

Intracellular acidification of the oocytes was produced using two methods:

superfusion with a solution enriched in $CO_2$ which produces acidification by a mechanism involving the bicarbonate transport system (Guillemare, E. et al., 1995, Mol. Pharmacol., 47, 588–594);

treatment with dinitrophenol (DNP), which is a metabolic inhibitor that decouples the H+ gradient in mitochondria and induces internal acidity (Pedersen, P. L. and Carafoli, E., 1987, Trends Biol. Sci., 12, 146–189).

Figure 6A:
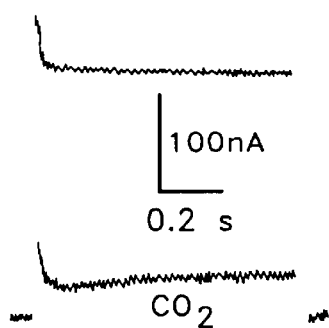
FIGS. 6(a–h) shows the blocking of the TWIK-1 channels by the internal pH. (a and b): blocking effect of the internal acidification on the TWIK-1 currents, induced by perfusion of $CO_2$; (a) tracings of superimposed currents induced by a depolarization phase at –30 mV starting at HP=–80 mV, control (top tracing), effect when equilibrium is reached in the presence of $CO_2$ (bottom tracing); (b): graph (n=5) showing the almost complete blockade of the TWIK-1 currents induced by CO2; (c and d): internal acidification induced by the application of DNP (1 mM). (c): same protocol as in (a), control (top tracing) and after 5 minutes of application of DNP (bottom tracing); (d): graph (n=4) indicating the percentage of TWIK-1 current remaining after treatment with DNP. (e and f): imposed voltage (method: attached patch) under symmetrical conditions of K+ concentration (140 mM) maintained at +80 mV. (e) course over time of the effect of 1 mM of DNP (marked with arrow) on the activities of the single TWIK-1 channel. (f): graph (n=4) showing the effect of DNP on the mean probability of opening $NP_0$ calculated during 1 minute of recording starting at the equilibrium state. (g): activities measured in the "inside-out patch" state at 80 mV at different internal pH values. Bar graph (n=10) of $NP_0$ in relation to the internal pH.
Figure 6B:
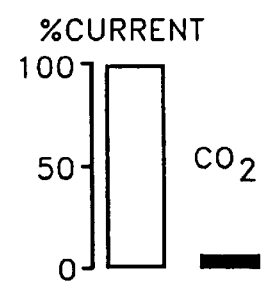
Figure 6C:
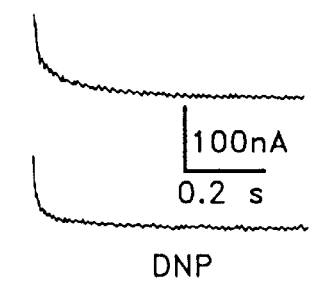
Figure 6D:
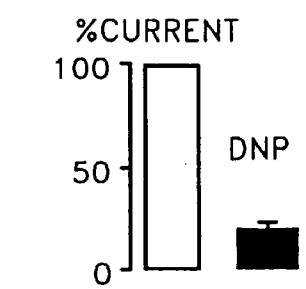
Figure 6E:
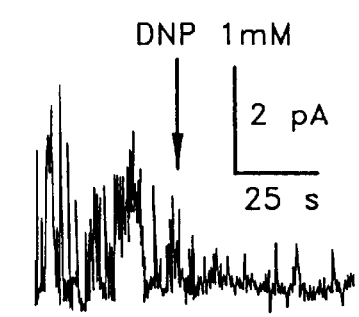
Figure 6F:
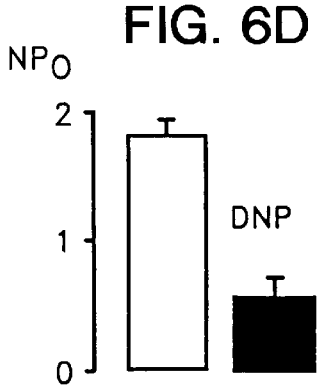
Figure 6G:
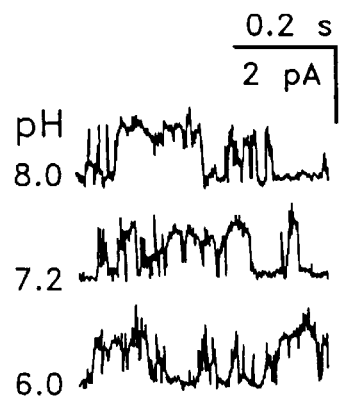
Figure 6H:
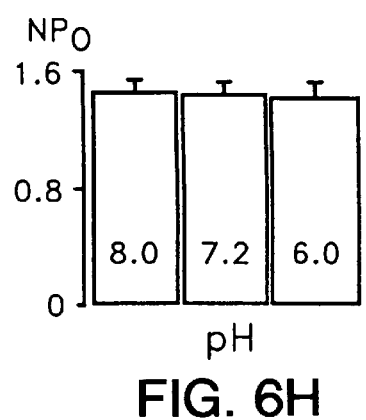

Both of these experimental methods resulted in a significant reduction in the TWIK-1 currents, greater than 95% in the case of $CO_2$ and 80% in the case of DNP of the control amplitude values, as shown in FIGS. 6a to 6d. The inhibition induced by DNP on the activity of the single K+ channel was again observed under the attached patch conditions, as shown in FIGS. 6e to 6f. However, after excision of the patch, the activity of the channel became insensitive to the acidification of the internal solution produced either by modifying the $Na_2HPO_4/NaH_2PO_4$ buffer ratio (FIGS. 6g and 6h 3 or by bubbling of $CO_2$ (not shown). Thus, the effect of the pH value on the activity of the TWIK-1 channel is probably indirect.

Figure 7A:
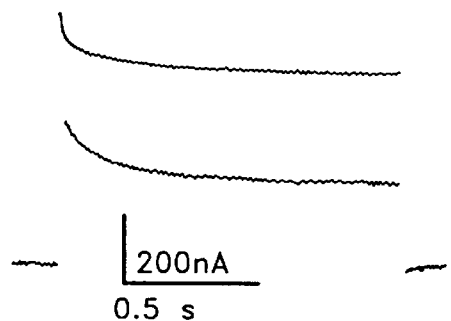
FIGS. 7(a–d) shows the activation of the TWIK-1 channels by PMA, activator of protein kinase C. (a): perfusion of PMA (30 nM) for 10 minutes increases the TWIK-1 current (top tracing) induced by a depolarization phase at +30 mV starting at HP=–80 mV, control current (top tracing). (b): graph (n=5) showing the activation effect of PMA on the TWIK-1 currents. (c and d): attached patch configuration under symmetrical K+concentration conditions maintained at +60 mV; (c): course over time of the effect of 30 nM of PMA on the single channel activities; the recordings of the channel activity were performed with a rapid scanning before and after the application of PMA; (d): bar graph (n=5) showing the activation effect of PMA on $NP_0$.
Figure 7B:
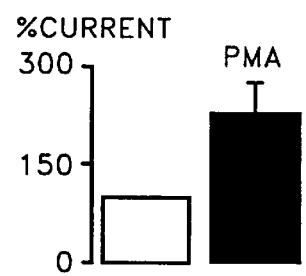
Figure 7C:
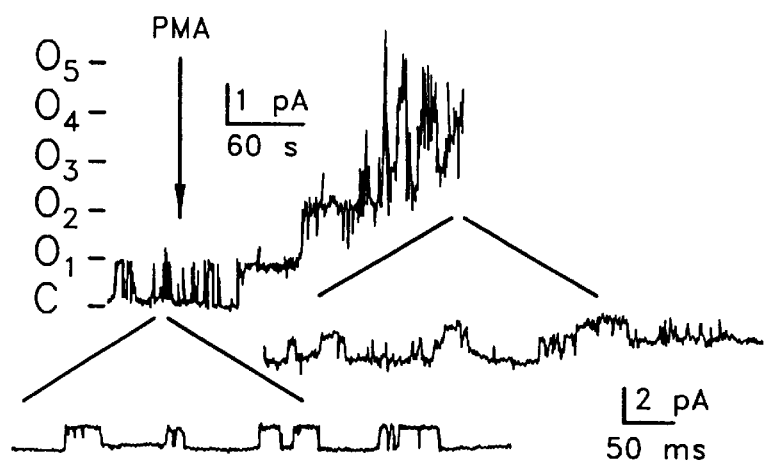
Figure 7D:
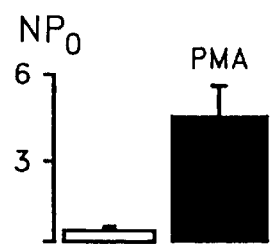

Phosphorylation or dephosphorylation of specific amino acid residues is an important mechanism of regulation of the ionic channels (Levitan, I. B., 1994, Annul Rev. Physiol., 56, 193–212). As shown in FIG. 7, activation of protein kinase C by phorbol-12 myristate acetate (PMA, 30 nM) increases the TWIK-1 currents. The inactive phorbol ester 4α-phorbol-12, 13 didecanoate (PDA, 1 μM) has no effect. In an attached patch which initially expressed solely a single channel, application of PMA showed the presence of at least five channels (FIGS. 7c and 7d). This experiment shows that at least four channels are silently present in the patch before the application of PMA. Since the TWIK-1 sequence contains a consensus phosphorylation site for protein kinase C (PKC), located at the level of the threonine in position 161 (FIG. 1b), the effect of PMA suggests regulation under the control of PKC. However, the in mutation of the threonine 161 into alanine leads to a muted channel which remains functional and conserves the capacity to be activated by PMA.

Activation of protein kinase A by application of 8-Cl-AMPc (300 μM) or forskolin (10 μM) does not affect the activity of TWIK-1. Elevation of the cytoplasmic $Ca^{2+}$ concentration by application of A23187 (1 μM) which could be activated by Ca2+-calmodulin kinase II and/or reveal the presence of a channel activated by the $Ca^{2+}$, is also without effect on the properties of the TWIK-1 channel.

Figures 9A, 9B:
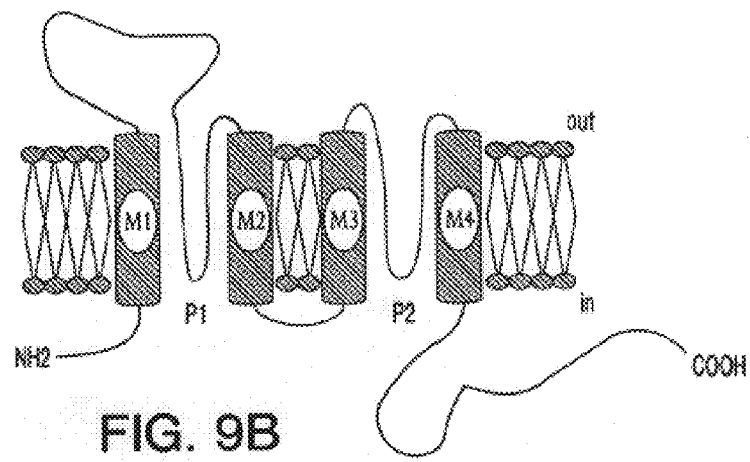
FIGS. 9(A–B) shows the sequence comparison and membrane topology of TWIK-related channels. A: Alignment of human TWIK-1 (SEQ ID NO:2), mouse TREK-1 (SEQ ID NO:8) and human TASK (SEQ ID NO:4) sequences. Identical and conserved residues are shown in black and grey, respectively. Dashes indicate gaps introduced for a better alignment. Relative positions of putative transmembrane segments (M1 to M4) and P domains (P1 and P2) of human TASK are also indicated. The M1–M4 domains were deduced from a hydropathy profile computed with a window size of 11 amino acids according to the Kyte and Doolittle method (Kyte and Doolittle, 1982). B: Putative membrane topology of TWIK-1, TREK-1 and TASK channels.

Cloning and Primary Structure of TASK, Another Member of the TWIK-related K+ Channel Family TWIK-1 and TREK-1 sequences were used to search related sequences in GenBank database by using the Blast alignment program. There were identified two mouse Expressed Sequence Tag (EST, accession numbers W36852 and W36914) that overlap and give a contig fragment of 560 bp whose deduced amino acid sequence presents significant similarity with TWIK-1 and TREK-1. A corresponding DNA fragment was amplified by RT-PCR and used to screen a mouse brain cDNA library. Eight independent clones were isolated. The 1.8 kb cDNA insert of the longer one bears in its 5' part an open reading frame (ORF) coding for a 405 amino acids polypeptide (SEQ ID NO:5) (FIG. 8). This ORF does not begin with an initiating methionine codon suggesting that the brain cDNA clones were partial. Ten additional positive clones were isolated from a mouse heart cDNA library. Analysis of their 5' sequence showed that all these clones were not longer than the clones previously isolated from brain. The 5' sequence has a very high GC content and is probably associated to secondary structures that could have promoted prematurate stops of RNA reverse transcription during the construction of both mouse cDNA libraries. To overcome this problem, the complete CDNA was cloned in another species. The DNA probe was used to screen a cDNA library from human kidney, a tissue that express both TWIK-1 and TREK-1 channels. Two hybridizing clones were characterized. Both contain an ORF of 1185 nucleotides encoding a 394 amino acids polypeptide (SEQ ID NO:3 and SEQ ID NO:4) (FIG. 8). The human protein sequence contains consensus sites for N-linked glycosylation (residue 53), and phosphorylation by protein kinase C (residues 358 and 383), tyrosine kinase (residue 323) and protein kinase A (residues 392 and 393). All these phosphorylation sites are located in the C-terminus part of the protein. Except for a 19 residues cluster (aa 276 to 294 in the human sequence), mouse and human proteins share a high overall sequence conservation (85% of identity) indicating that they probably are products of ortholog genes (FIG. 8). Sequence alignments presented in FIG. 9 clearly show that the cloned protein is a new member of the TWIK related K+ channel family. Like TWIK-1 (SEQ ID NO:2) and TREK-1 (SEQ ID NO:8), TASK (SEQ ID NO:4) has four putative transmembrane segments (M1 to M4) and two P domains (P1 and P2) (FIGS. 9A and 9B). TASK is 58 amino acids longer than TWIK-1 and 24 amino acids longer than TREK-1 because its C-terminus is more extended.

Distribution of TASK

Figure 10:
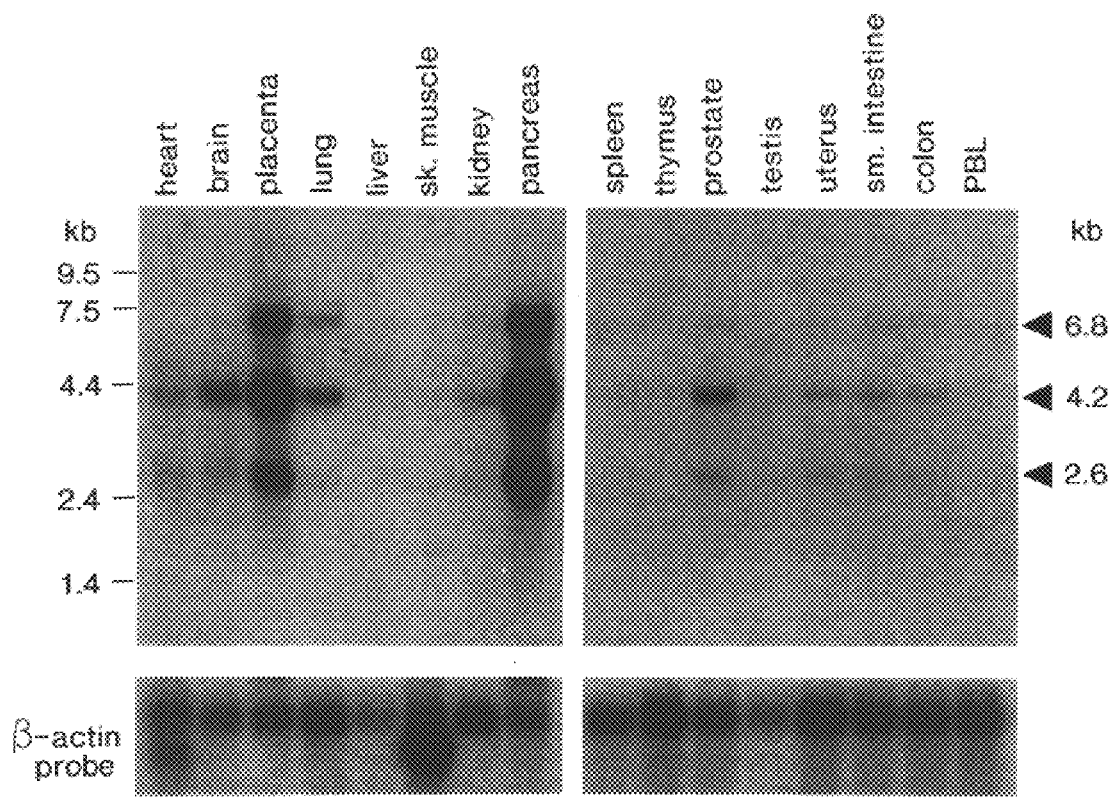
FIG. 10 shows the northern blot analysis of TASK distribution in adult human tissues. Human multiple tissues Northern blots from Clontech were probed at high stringency with a TASK cDNA probe. Each lane contains 2 $\mu$g of poly(A)+ RNA. Autoradiograms were exposed for 48 h at –70° C. The blots were re-probed with a $\beta$-actin cDNA probe for control. sk. muscle: skeletal muscle, sm. intestine: small intestine, PBL: peripheral blood leukocytes.

The expression of TASK in adult human and mouse tissues was examined by Northern blot analysis. Three different transcripts were detected in the human tissues with estimated sizes of 6.8, 4.2 and 2.6 kb (FIG. 10), the shorter one having the same size that the cloned cDNAs. The two other transcripts (4.2 and 6.8 kb) may result from alternate polyadenylation signals in the 3' non-coding sequence and/or correspond to alternatively spliced or immature forms of the transcript. TASK is expressed in many different tissues but is particularly expressed in pancreas and placenta. Lower levels of expression were found in the brain>lung, prostate>heart, kidney>uterus, small intestine and colon. As shown in FIG. 11A, the TASK probe detected a single transcript in the mouse with an estimated size of 4.2 kb. TASK is expressed in the heart>lung>brain and kidney. No expression was seen in liver and skeletal muscle. The TASK distribution was further studied in adult mouse brain and heart by in situ hybridization. A wide and heterogeneous pattern of expression was obtained in the brain (FIGS. 11B and 11C). TASK mRNA was detected throughout the cell layers of the cerebral cortex, in the CA1–CA4 pyramidal cell layer, in the granule cells of the dentate gyrus, in the habenula, in the paraventricular thalamic nuclei, in the amyloid nuclei, in the substantia nigra and in the Purkinje and granular cells of the cerebellum. In the heart, a high level of TASK expression was found in the atria (FIG. 11D) while ventricular cells did not express this channel.

The TASK distribution was further studied in adult mouse brain and heart by in situ hybridization. In situ hybridization experiments were performed on adult Balb/c mice by using standard procedures (Fink et al, 1996b). An antisense oligonucleotide (48 mer, 5'-CACCAGCAGGTAGGTGAAGGTGCACACGATG AGAGCCAACGTGCGCAC-3') complementary (SEQ ID NO:24) to the mouse cDNA sequence of TASK (from nucleotides 7 to 54) was used to detect the expression of TASK transcripts in frozen fixed brain sections (10 $\mu$m). The probe was 3'-end-labelled with ($\alpha$-$^{33}$P)dATP. Sections were digested with 5 $\mu$g/ml of proteinase K for 15 min at 37° C., acetyled for 10 min in 0.25% acetic anhydre in 0.1 M triethanolamine. Hybridization was carried out overnight at 37 ° C in 2×SSC, 50% formamide, 10% dextran sulfate, 1×Denhardt's solution, 5% sarcosyl, 500 $\mu$g denatured salmon sperm DNA, 250 mg/nl yeast tRNA, 20 mM dithiothreitol, and 20 mM NaPO$_4$ with 0.2 ng/ml of radio-labelled probe (specific activity=8.10$^8$ dpm/$\mu$g). Slides were then washed in 1×SSC before dehydratation, drying, and apposition to hyperfilm-$\mu$max (Amersham) for 6 days. The specificity of labelling was verified by in situ hybridization using cold displacement of radioactive probe with a 500-fold excess of unlabelled oligonucleotide.

Biophysical Properties Of Task Currents

For functional studies, TASK cRNAs were injected into *Xenopus oocytes*. This was accomplished by subdloning a 2480 bp SmaI/XhoI fragment from pBS-hTASK containing 14 bp of 5' UTR, the coding sequence and the entire 3' UTR into the pEXO vector (Lingueglia et al., 1993) to give pEXO-TASK. Capped-cRNAs were synthesised in vitro from the linearized plasmid by using the T7 RNA polymerase (Stratagene). Xenopus laevis were purchased from CRBM (Montpellier, France). Preparation and cRNA injection of oocytes has been described elsewhere (Guillemare et al., 1992). Oocytes were used for electrophysiological studies 2 to 4 days following injection (20 ng/oocyte). In a 0.3 ml perfusion chamber, a single oocyte was impaled with two standard microelectrodes (1–2.5 M$\Omega$ resistance) filled with 3 M KCl and maintained under voltage clamp by using a Dagan TEV 200 amplifier, in standard ND96 solution (96 mM NaCl, 2 mM KCI, 1.8 mM CaCl$_2$, 2 mM MgCl$_2$, 5 mM HEPES, pH 7.4 with NaOH). In some experiments, NaCl was substituted with TMA Cl (Tetra Methyl Ammonium Chloride). Stimulation of the preparation, data acquisition, and analysis were performed using pClamp software (Axon instruments, USA). Drugs were applied externally by addition to the superfusate (flow rate: 3 ml/min) or intracellularly injected by using a pressure microinjector (Inject+Matic, Switzerland). All experiments were performed at room temperature (21–22° C.).

Figure 12A:
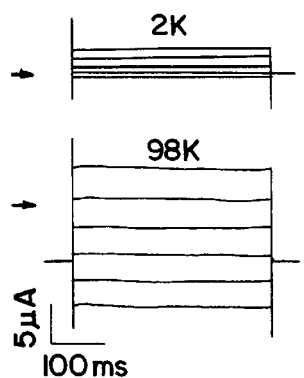
FIGS. 12(A–F) shows the biophysical properties of TASK in Xenopus oocytes and COS cells. A: TASK currents recorded from a Xenopus oocyte injected with TASK cRNA and elicited by voltage pulses from −150 mV to +50 mV in 40 mV steps, 500 ms in duration, from a holding potential of −80 mV in low (2 mM K$^+$) or high K$^+$ solutions (98 mM K$^+$). The zero current level is indicated by an arrow. B: Current-voltage relationships. Mean currents were measured over the last 50 ms at the end of voltage pulses from −150 to +50 mV in 10 mV steps as in A. Modified ND96 solutions containing 2 mM K$^+$ and 96 mM TMA were used, TMA was then substituted by K$^+$ to obtain solutions ranging from 2 mM to 98 mM K$^+$. TASK currents are not sensitive to external TMA, no changes were observed upon substitution of NaCl by TMA (data not shown). C: Upper panel: reversal potentials of TASK currents as a function of external K$^+$ concentration (mean ±SEM, n=3). Lower panel: slope conductance measured between +10 and +50 mV on current-voltage relations as in A, plotted as a function of the external K$^+$ concentration (mean ±SEM, n=3). The mean values were fitted with an hyperbola function. D: Theoretical current-voltage relation in the same conditions as in A calculated according to the following modified Goldman-Hodgkin-Katz (GHK) current relationship.
Figure 12B:
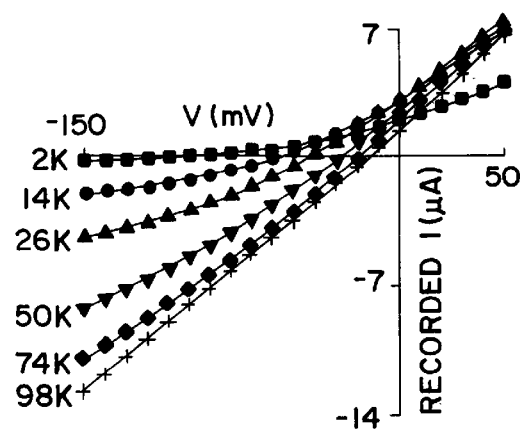
Figure 12C:
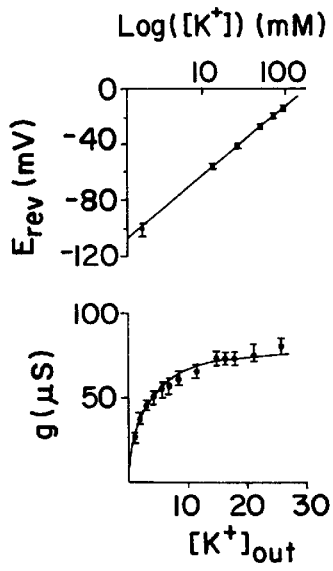
Figure 12D:
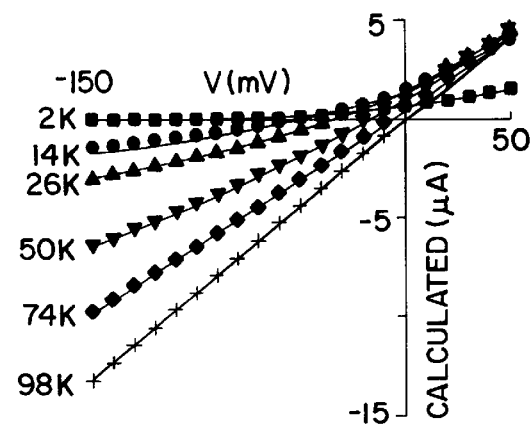

A non-inactivating current, not present in uninjected oocytes (not shown), was measured by two-electrode voltage-clamp (FIG. 12A). Activation kinetics of the TASK current are almost instantaneous (under 10 ms). The current-voltage (I–V) relationship is outwardly-rectifying and almost no inward currents were recorded in the ND96 external medium containing 2 mM K$^+$ (FIG. 12B). However, inward currents were revealed when the external K$^+$ concentration ([K$^+$]$_{out}$) was gradually mincreased to 98 mM K$^+$ (FIGS. 12A and 12B). FIG. 12A presents the I–V relationships of the current in K$^+$-rich solutions ranging from 2 mM to 98 mM. The relationship between the reversal potential and [K$^+$]$_{out}$ was close to the predicted Nernst value (52.1 mV/decade, n=4) as expected for highly selective K$^+$ channel (FIG. 12C, upper panel). On the other hand, external K$^+$ enhanced the outward currents in a concentration-dependent manner as illustrated in FIG. 12C (lower panel). The half maximum activation by K$^+$ was observed at a K$_{0.5}$ of 2.06 mM. The theoretical I–V relationships in various [K$^+$]$_{out}$ calculated according to the Goldman-Hodgkin-Katz current equation are shown in FIG. 12D. These I–V relationships are very close to the I–V relationships corresponding to recorded TASK currents (FIG. 12A). This strongly suggests that TASK currents show no rectification other than that predicted from the constant-field assumptions and that TASK lacks intrinsic voltage-sensitivity. The slight deviation between experimental and theoretical points are probably due to small endogenous chloride conductance and/or a K$^+$ loading of the oocytes. It has been previously shown that oocytes expressing TWIK-1 or TREK-1 are more polarized that control oocytes, the resting membrane potential (E$_m$) reaching a value close to the K$^+$ equilibrium potential (E$_K$). In oocytes expressing TASK, E$_m$ was –85±0.8 mV (n=23, in standard ND96) instead of –44±2.6 mV (n=9) in non-injected oocytes. This result demonstrates that TASK, like other TWIK or TREK channels, is able to drive E$_m$ close to E$_K$. The effect of various pharmacological agents on currents elicited by voltage pulses to +50 mV has been studied in TASK-expressing oocytes. Less than 20% of TASK currents were inhibited in the presence of quinine (100 $\mu$M), quinacrine (100 $\mu$M) or quinidine (100 $\mu$M). The "classical" K$^+$ channels blockers tetraethylammonium (TEA, 1 mM) and 4-aminopyridine (4AP, 1 mM) were also inactive. Cs$^+$ (100 $\mu$M) induced a voltage-dependent block of 31±2% (n=4) of the inward current, recorded at –150 mV, in 50 mM external K$^+$. In the same conditions, Ba$^{2+}$ (100 $\mu$M) was ineffective with a variation of 6±1% (n=4) of the inward current.

Biophysical Properties of TASK Channel in Transfected COS Cells

The 2480 bp SmaI/XhoI fragment of pBS-TASK was subcloned into the pCi plasmid (Promega) under the control of the cytomegalovirus promoter to give pCi-TASK. COS cells were seeded at a density of 70,000 cells per 35 mm dishes 24 h prior transfection. Cells were then transfected by the classical calcium phosphate precipitation method with 2 $\mu$g of pCI-TASK and 1 $\mu$g of CD8 plasmids. Transfected cells were visualized 48 h after transfection using the anti-CD8 antiboby coated beads method (Jurman et al., 1994). For electrophysiological recordings, the internal solution contained 150 mM KCl, 3 mM MgCl$_2$, 5 mM EGTA, and 10 mM HEPES at pH 7.2 with KOH, and the external solution 150 mM NaCl, 5 mM KCl, 3 mM MgCl$_2$, 10 mM HEPES at pH 7.4 with NaOH.

Figure 12E:
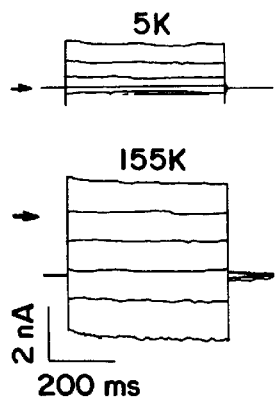
Figure 12F:
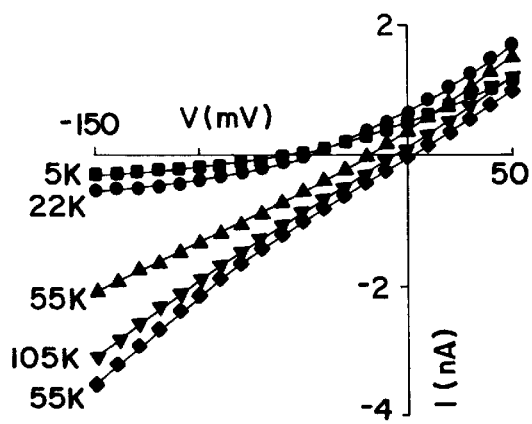

Untransfected cells did not express this K$^+$ channel activity (not shown). FIG. 12E shows whole cell currents recorded in the mammalian COS cells transiently transfected with TASK, in external solutions containing 5 mM and 155 mM K$^+$. The current were instantaneous and non-inactivating as in *Xenopus oocytes*. FIG. 12F presents the I–V relationships of TASK current in various external K$^+$ concentrations. The currents show the same Goldman-Hodgkin-Katz type outward rectification as in oocytes.

Regulation of the TASK Channel

Figure 13A:
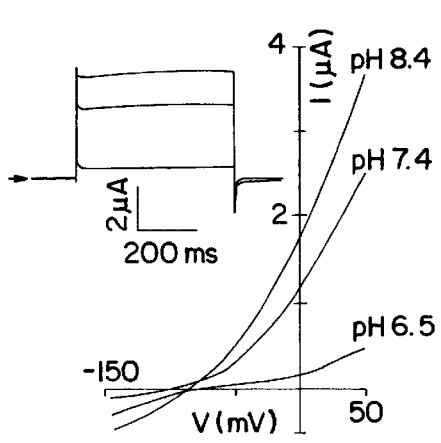
Figure 13B:
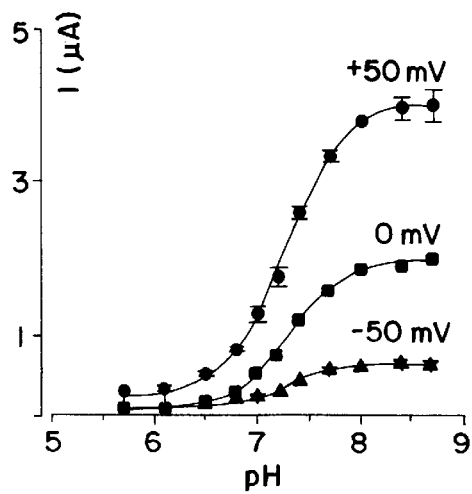
Figure 13C:
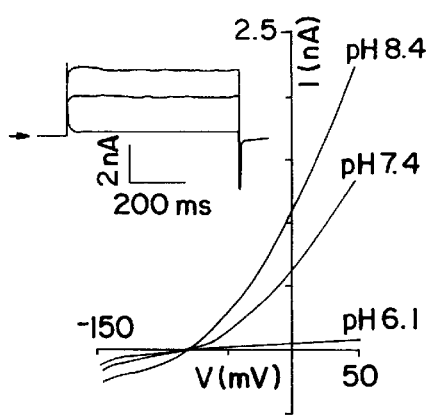
Figure 13D:
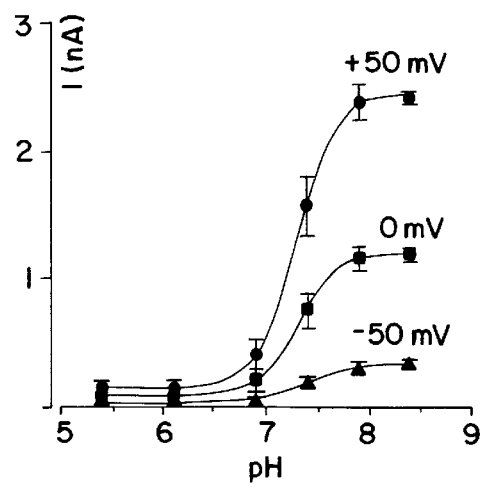

TASK currents were insensitive to internal Ca$^{2+}$ changes obtained by injection of inositol triphosphate (IP3, 1 mM) or EGTA (100 mM), to the activation of adenyl cyclase by perfusion of IBMX (1 mM) and forskolin (10 μM), or to the activation of protein kinase C (PKC) by application of the phorbol ester PMA (40 nM). TASK currents were insensitive to the internal acidification or alkalisation obtained by injection of solutions at pH 2 or 8.7 respectively (n =3). However, their very interesting property is that they are highly sensitive to external pH. The current-potential relationships recorded from a TASK-expressing oocyte at pH 6.5, 7.4 and 8.4 are presented in FIG. 13A. For an external pH of 6.5, a drastic block was observed at all potentials while an activation was recorded at pH 8.4, also at all potentials. The inhibition and activation produced no modification of current kinetics (FIG. 13A, inset). The pH-dependence of the TASK channel is shown in FIG. 13B. For currents recorded at +50 mV, the inhibition by acidic pHs was characterised by an apparent pK of 7.34±0.04 units (n=3) and a Hill coefficient of 1.54±0.08 (n=3). For currents recorded at 0 and −50 mV, the pKs were 7.32±0.02 and 7.30±0.01 respectively (n=3) showing that the blocking effect of external protons is not voltage-dependent. The resting membrane potential of TASK-expressing oocytes was −84±1 mV (n=6) at pH 7.4 and shifted to −47±6 mV (n=6) at pH 6.4 (not shown). Finally, FIGS. 13C and 13D show that the strong pH sensitivity of TASK currents was also observed in transfected COS cells. A large inhibition or activation of the current was recorded, at all potentials, when pH was changed from 7.4 to 6.1 or 7.9 respectively (FIG. 13C). The kinetics of the current were unmodified at both pH (FIG. 6C, inset). FIG. 13D shows that the pH effects were also non voltage-dependent in COS cells. The external pH-dependence of TASK, at +50 mV, indicates a pK value of 7.29±0.03 (n=5) and a Hill coefficient of 1.57±0.07 (n=5). Currents recorded at 0 and |50 mV presented pKs of 7.29±0.04 (n=5) and 7.32±0.05 (n=4) respectively. 10% of the maximum current was obtained at pH 6.68±0.08 (n=4) and 90% at pH 7.66±0.05 (n=4). These results confirm that TASK is extremely sensitive to extracellular pH in the physiological range.

Other Homologs of TWIK-1

Comparison of the complete sequence of TWIK-1 with the sequences of the Genbank data base allowed identification of at least five genes of *Caenorhabditis elegans*, which had been characterized in the context of the Nematode Sequencing project, which may encode additional structural homologues of TWIK-1. The alignment of two of these homologues (SEQ ID NO:7 and SEQ ID NO:6) with TWIK-1 (SEQ ID NO:2) is shown in FIG. 2b. The degree of similarity between the deduced protein sequences of *C elegans* and TWIK-1 are approximately 55 to 60%. Amino acid sequence identities among the deduced polypeptide sequences range from 25 to 28%. Interestingly, the degree of similarity and amino acid sequence identity of the various *C elegans* are not greater than what was determined for TWIK-1. These results indicate that other TWIK-1 relates potassium channels may be present in the *C elegans* genome and suggest that additional members of the TWIK-1 famiy of potassium channels may exist in mammals.

Unique Structural Features of TWIK-1 and TASK Family of Potassium Transport Channels This invention describes the isolation and the characterization a novel human $K^+$ channel. This channel has an overall structural similarity with TWIK-1 and TREK-1 channels that suggests a common ancestral origin. Despite this similar structural organization, the amino acid identity between TASK and the two other mammalian related channels is very low (25–28%). Sequence homologies are no higher between TASK and a recently cloned Drosophila channel that also belongs to the structural TWIK channel class (Goldstein et al., 1996). The highest degree of sequence conservation is in the two P domains and the M2 segment. In these regions the amino acid identity reaches ~50%. Like other TWIK-related channels, TASK contains an extended M1P1 interdomain. This peculiar domain has been shown to be extracellular in the case of TWIK-1 and to be important for the self-association of two TWIK-1 subunits. The TWIK-1 homodimers are covalent because of the presence of an interchain disulfide bridge between cysteines 69 located in the M1P1 interdomain (Lesage et al., 1996b). This particular cysteine residue is conserved in TREK-1 (residue 93) (SEQ ID NO:8) but not in TASK strongly suggesting that TASK probably does not form covalent dimers as observed for TWIK1 (Lesage et al., 1996b) and TREK-1 (unpublished data).

The biophysical and regulation properties of TASK are unique. TWIK-1 has a mild inward rectification that involves an internal block by $Mg^{2+}$ (Lesage et al., 1996a). TREK-1 expresses an outward rectification which seems to result from a voltage-sensitivity intrinsic to the channel protein (Fink et al., 1996b). In the case of TASK, the outward rectification observed at physiological external $K^+$ concentrations can be approximated to the rectification predicted by the Goldman-Hodgkin-Katz current equation suggesting that this rectification simply results from the asymmetric concentrations of $K^+$ on both sides of the membrane. In other words, this would mean that TASK lacks intrinsic voltage-sensitivity and behaves like a $K^+$-selective "hole". This behavior is unique among cloned mammalian $K^+$ channels to the inventors' knowledge. Voltage- and time-independences are classical criteria to describe the so-called leak or background $K^+$ channels. Some of these channels have been described in invertebrates, the best characterized of which being the S channels in Aplysia sensory neurones (Siegelbaum et al., 1982) and in vertebrates, for example in bullfrog sympathetic ganglia (Koyano et al., 1992), guinea-pig submucosal neurons (Shen et al., 1992), rat carotid bodies (Buckler, 1997), and guinea-pig ventricular myocytes (Backx and Marban, 1993). These channels are open at all membrane potentials and probably play a pivotal role in the control of the resting membrane potential and in the modulation of electrical activity of both neurones and cardiac cells. However, their lack of kinetics, voltage- and time-sensitivities, and their absence of a specific pharmacology has delayed their extensive electrophysiological and physiological characterization. Cloning of TASK, the first "true" background mammalian $K^+$ channel should help to better characterize this peculiar functional family of $K^+$ channels at the molecular level and identify specific and high affinity pharmacological agents that would block these channels and would facilitate analysis of their physiological roles.

TASK behaves as a $K^+$-selective "hole" but this does not mean that its activity cannot be modulated. Unlike TWIK-1 and TREK-1 channels, its activity is not changed by activation of protein kinase A or C (Fink et al., 1996b; Lesage et al., 1996a). The probably very important property of TASK is that it is extremely sensitive to extracellular pH in the physiological range i.e. between 6.5 and 7.8. The Hill coefficient of ~1.6 found for the $H^+$ concentration dependence of the TASK current is consistent with the idea that the channel is formed by the assembly of 2 subunits as previously in demonstrated for TWIK1. These 2 subunits would be in strong cooperative interactions in regards to H$^+$.

The modulation by external protons probably has important implication for the physiological function of the TASK channel. Stimulus elicited pH shifts have been characterized in a wide variety of neural tissues by using extracellular pH-sensitive electrodes (reviewed in (Chesler, 1990; Chesler and Kaila, 1992)). They can be observed in physiopathological situations such as epileptiform activity and spreading depression in which acid shifts are usually preceded by alkaline transients (Siesjö et al., 1985; Nedergaard et al., 1991). They can be observed of course in ischemia where large acidifications of the extracellular medium have been recorded (Kraig et al., 1983; Mutch and Hansen, 1984). However, they can also be observed in physiological conditions such as electrical stimulation of Schaeffer collateral fibers in the hippocampal slice (Krishtal et al., 1987), or light stimulation of the retina (Borgula et al., 1989; Yamamoto et al., 1992), or parallel fibers in cerebellum (Kraig et al., 1983). All these pH-shifts correspond to bursts of H$^+$ or OH$^-$ creating small pH variations from the external physiological pH value of 7.4 in the alkaline or acidic direction (up to 0.3 pH units) and are rapid, in the second to 30 seconds range. They might actually be larger in range or shorter in time course in the vicinity of the synaptic cleft. A particularly interesting issue is whether these relatively small activity-dependent pH changes have significant modulatory effects. In other words, does H$^+$ serve a transmitter role in the nervous system? The discovery of this new TASK channel that can fully open or close within a range of only 0.5 pH unit around the physiological pH (7.4) will certainly strengthen the idea that pH could be a natural modulator of neuronal activity (Chesler and Kaila, 1992).

From the above description it will seem that the present invention relates to an isolated, purified nucleic acid molecule that codes for a protein constituting a potassium channel of the TWIK-1 family or exhibiting the properties and structure of the type of the TWIK-1 channel described above.

More specifically, the said nucleic acid molecule codes for the TWIK-1 protein, the amino acid sequence of which is represented in the attached sequence list as number SEQ ID NO:2, or TASK, represented in the attached sequence list as number SEQ ID NO:4, or functionally equivalent derivatives of these sequences that possess the distinguishing structural features of the TWIK-1 family of potassium transport proteins. Such derivatives can be obtained by modifying and or suppressing one or more amino acid residues of this sequence, as long as this modification and/or suppression does not modify the functional properties of the TWIK-1 potassium channel of the resultant protein. sequence of a DNA molecule coding for this protein is more specifically the molecule coding for TWIK-1, represented in the attached sequence list as number SEQ ID NO:1 or TASK, represented in the attached sequence list as number SEQ ID NO:3.

The invention also relates to a vector containing a molecule of the aforementioned nucleic acid sequences, as well as a procedure for production or expression in a cellular host of a protein constituting a TWIK-1 potassium channel or a channel of the same family as TWIK-1.

A procedure for production of a protein constituting a TASK potassium channel or exhibiting the properties and structure of the type of the TASK channel composes transferring a nucleic acid molecule of the invention or a vector containing the said molecule into a cellular host, culturing the transformed cellular host obtained in the preceding step under conditions enabling the production of potassium channels exhibiting the properties of TASK, and isolating the proteins constituting the potassium channels of the TASK family.

A procedure for the expression of a TASK potassium channel or a potassium channel of the same family as TASK comprises transferring a nucleic acid molecule of the invention or a vector containing the said molecule into a cellular host, and culturing the cellular host obtained under conditions enabling the expression of potassium channels of the TASK family. The cellular host employed can be selected from among the prokaryotes or the eukaryotes, and notably from among the bacteria, the yeasts, mammal cells, plant cells or insect cells. The vector used is selected in relation to the host into which it will be transferred; it can be any vector such as a plasmid. The invention also relates to the transferred cells expressing the potassium channels exhibiting the properties and structure of the type of the TASK channel obtained in accordance with the preceding procedures.

The cells expressing TASK potassium channels or channels exhibiting the properties and structure of the type of the TASK channels obtained in accordance with the preceding procedures are useful for the screening of substances capable of modulating the activity of the individual members of the TASK family of potassium channels. This screening is carried out by bringing into contact variable amounts of a substance to be tested with cells expressing the TASK channel or potassium channels exhibiting the properties and structure of the type of the TASK channels, then determining the effects of said substance on the currents of the potassium channels of these channels.

This screening procedure makes it possible to identify drugs that may be useful in the treatment of diseases of the heart or of the nervous system. Diseases involving the potassium channels and thus likely to involve the channels of the TASK family are, for example, epilepsy, heart (arrhythmias) and vascular diseases, neurodegenerative diseases, especially those associated with ischemia or anoxia, the endocrine diseases associated with anomalies of hormone secretion, muscle diseases.

An isolated, purified nucleic acid molecule coding for a protein of the TASK family of potassium channel or a vector including this nucleic acid molecule or a cell expressing the potassium channel polypeptide, are also useful for the preparation of transgenetic animals. These can be animals supra-expressing said channels, but especially so-called knock-out animals, i.e., animals presenting a deficiency of these channels; these transgenetic animals are prepared by methods known to the experts in the field, and enable the preparation of live models for studying animal diseases associated with the TASK family of channels.

The nucleic acid molecules of the invention or the cells transformed by said molecule can be used in genetic therapy strategies to compensate for a deficiency in the potassium channels at the level of one or more tissues of a patient. The invention thus also relates to a medication containing nucleic acid molecules of the invention or cells transformed by said molecule for the treatment of disease involving the potassium channels.

The present invention also has as its object a new family of K+ channels, of which TWIK-1 and TASK are members, which polypeptides are present in most human tissues, but especially abundant in the brain and the heart, and which exhibit the properties and structure of the type of those of the TWIK-1 channels described above. Thus, the invention relates to an isolated, purified protein whose amino acid sequence is represented in the attached sequence list as (SEQ ID NO:3) SEQ ID NO:4 or SEQ ID NO:5, or a functionally equivalent derivative of these sequences. Such derivatives can be obtained by modifying and/or suppressing one or more amino acid residues of this sequence or by segmenting this sequence, as long as this modification and/or suppression or deletion of a fragment does not modify the functional properties of the TASK type potassium channel of the resultant protein.

Proteins comprising a TASK type potassium channel are useful for the manufacture of medications intended for the treatment or prevention of diseases involving dysfunction of the potassium channels.

Polyclonal or monoclonal antibodies directed against a protein constituting a TASK type potassium channel can be prepared by conventional methods described in the literature. These antibodies are useful for investigating the presence of potassium channels of the TASK family in different human or animal tissues, but can also be applied for the in vivo inhibition or activation of TASK type potassium channels.

Materials and Methods

Cloning of TASK and RNA Analysis

TWIK-1 and TREK-1 were used to search homologues in gene databases by using the tBlastn sequence alignment program (Altschul et al., 1990). Translation of two overlapping EST sequences (GenBank accession numbers W36852 and W36914) in one frame presented significant sequence similarities with TWIK-1 and TREK-1. A 560 bp DNA fragment was amplified by PCR from mouse brain poly(A)$^+$ cDNAs and subcloned into pBluescript (Stratagene) to give pBS-852/914. This fragment was $^{32}$P-labelled and used to screen mouse brain and heart cDNA libraries. Filters were hybridized and washed as previously described (Fink et al., 1996b). Eight positive clones from brain and ten from heart were obtained. CDNA inserts were characterized by restriction analysis and by partial or complete sequencing on both strands by the dideoxy nucleotide chain termination method using an automatic sequencer (Applied Biosystems). All the clones were shown to only contain a partial ORF. The cDNA insert of the longer mouse clone (designated pBS-mTASK) was $^{32}$P-labelled and used to screen a human kidney cDNA library. Two independent hybridizing clones were isolated and sequenced. Both clones (2.5 kb long) were shown to contain the full-length ORF. The longer one was designated pBS-hTASK.

For Northern blot analysis, poly(A)$^+$ RNAs were isolated from adult mouse tissues and blotted onto nylon membranes as previously described (Lesage et al., 1992). The blot was probed with the $^{32}$P-labelled insert of pBS-mTASK in 50% Formamide, 5×SSPE (0.9 M sodium chloride, 50 mM sodium phosphate (pH 7.4), 5 mM EDTA), 0.1% SDS, 5×Denhardt's solution, 20 mM potassium phosphate (pH 6.5) and 250 $\mu$g denatured salmon sperm DNA at 50° C. for 18 h and washed stepwise at 55° C. to a final stringency of 0.2×SSC, 0.3% SDS. For hybridization of human multiple tissues Northern blots from Clontech, the procedure was identical except that the probe was derived from pBS-hTASK. The cDNA insert of pBS-hTASK contains different repeat sequences (AluJb, MIR and (CGG)n) in the untranslated regions (UTR) and a SmaI/ApaI restriction fragment of 1390 bp spanning the coding sequence was chosen as a probe that does not contain these repeats.

The gene of the TASK channel has been located on chromosome 2p23 between W1-13615 and W1-6283. Lesage F. and Lazdunski M., Genomics 51, 1998, incorporated herein by reference in its entirety.

The algorithms used in the present text are FASTA, Pearson, W. R. and Lipman, D. J., Proc. Nat'l. Acad. Sci. USA 85, 2444–2448 (1998) and BLAST, Altschul, S. F. et al., Nucleic Acids Res. 25, 3389–3402 (1997), both publications being incorporated herein in their entirety.

SEQUENCE LISTING

```
<160> NUMBER OF SEQ ID NOS: 24

<210> SEQ ID NO 1
<211> LENGTH: 1894
<212> TYPE: DNA
<213> ORGANISM: Homo sapiens
<220> FEATURE:
<221> NAME/KEY: CDS
<222> LOCATION: (183)..(1190)
<220> FEATURE:
<223> OTHER INFORMATION: TWIK-1

<400> SEQUENCE: 1
gggcaggaag acggcgctgc ccggaggagc ggggcgggcg ggcgcgcggg ggagcgggcg      60
gcgggcggga gccaggcccg ggcggggcg ggggcggcgg ggccagaaga ggcggcgggc     120
cgcgctccgg ccggtctgcg gcgttggcct tggctttggc tttggcggcg gcggtggaga     180 ag atg ctg cag tcc ctg gcc ggc agc tcg tgc gtg cgc ctg gtg gag        227
   Met Leu Gln Ser Leu Ala Gly Ser Ser Cys Val Arg Leu Val Glu
   1               5                  10                  15 cgg cac cgc tcg gcc tgg tgc ttc ggc ttc ctg gtg ctg ggc tac ttg       275
Arg His Arg Ser Ala Trp Cys Phe Gly Phe Leu Val Leu Gly Tyr Leu
            20                  25                  30
```

```
ctc tac ctg gtc ttc ggc gca gtg gtc ttc tcc tcg gtg gag ctg ccc      323
Leu Tyr Leu Val Phe Gly Ala Val Val Phe Ser Ser Val Glu Leu Pro
            35                  40                  45 tat gag gac ctg ctg cgc cag gag ctg cgc aag ctg aag cga cgc ttc      371
Tyr Glu Asp Leu Leu Arg Gln Glu Leu Arg Lys Leu Lys Arg Arg Phe
        50                  55                  60 ttg gag gag cac gag tgc ctg tct gag cag cag ctg gag cag ttc ctg      419
Leu Glu Glu His Glu Cys Leu Ser Glu Gln Gln Leu Glu Gln Phe Leu
    65                  70                  75 ggc cgg gtg ctg gag gcc agc aac tac ggc gtg tcg gtg ctc agc aac      467
Gly Arg Val Leu Glu Ala Ser Asn Tyr Gly Val Ser Val Leu Ser Asn
80                  85                  90                  95 gcc tcg ggc aac tgg aac tgg gac ttc acc tcc gcg ctc ttc ttc gcc      515
Ala Ser Gly Asn Trp Asn Trp Asp Phe Thr Ser Ala Leu Phe Phe Ala
                100                 105                 110 agc acc gtg ctc tcc acc aca ggt tat ggc cac acc gtg ccc ttg tca      563
Ser Thr Val Leu Ser Thr Thr Gly Tyr Gly His Thr Val Pro Leu Ser
            115                 120                 125 gat gga ggt aag gcc ttc tgc atc atc tac tcc gtc att ggc att ccc      611
Asp Gly Gly Lys Ala Phe Cys Ile Ile Tyr Ser Val Ile Gly Ile Pro
        130                 135                 140 ttc acc ctc ctg ttc ctg acg gct gtg gtc cag cgc atc acc gtg cac      659
Phe Thr Leu Leu Phe Leu Thr Ala Val Val Gln Arg Ile Thr Val His
    145                 150                 155 gtc acc cgc agg ccg gtc ctc tac ttc cac atc cgc tgg ggc ttc tcc      707
Val Thr Arg Arg Pro Val Leu Tyr Phe His Ile Arg Trp Gly Phe Ser
160                 165                 170                 175 aag cag gtg gtg gcc atc gtc cat gcc gtg ctc ctt ggg ttt gtc act      755
Lys Gln Val Val Ala Ile Val His Ala Val Leu Leu Gly Phe Val Thr
                180                 185                 190 gtg tcc tgc ttc ttc ttc atc ccg gcc gct gtc ttc tca gtc ctg gag      803
Val Ser Cys Phe Phe Phe Ile Pro Ala Ala Val Phe Ser Val Leu Glu
            195                 200                 205 gat gac tgg aac ttc ctg gaa tcc ttt tat ttt tgt ttt att tcc ctg      851
Asp Asp Trp Asn Phe Leu Glu Ser Phe Tyr Phe Cys Phe Ile Ser Leu
        210                 215                 220 agc acc att ggc ctg ggg gat tat gtg cct ggg gaa ggc tac aat caa      899
Ser Thr Ile Gly Leu Gly Asp Tyr Val Pro Gly Glu Gly Tyr Asn Gln
    225                 230                 235 aaa ttc aga gag ctc tat aag att ggg atc acg tgt tac ctg cta ctt      947
Lys Phe Arg Glu Leu Tyr Lys Ile Gly Ile Thr Cys Tyr Leu Leu Leu
240                 245                 250                 255 ggc ctt att gcc atg ttg gta gtt ctg gaa acc ttc tgt gaa ctc cat      995
Gly Leu Ile Ala Met Leu Val Val Leu Glu Thr Phe Cys Glu Leu His
                260                 265                 270 gag ctg aaa aaa ttc aga aaa atg ttc tat gtg aag aag gac aag gac     1043
Glu Leu Lys Lys Phe Arg Lys Met Phe Tyr Val Lys Lys Asp Lys Asp
            275                 280                 285 gag gat cag gtg cac atc ata gag cat gac caa ctg tcc ttc tcc tcg     1091
Glu Asp Gln Val His Ile Ile Glu His Asp Gln Leu Ser Phe Ser Ser
        290                 295                 300 atc aca gac cag gca gct ggc atg aaa gag gac cag aag caa aat gag     1139
Ile Thr Asp Gln Ala Ala Gly Met Lys Glu Asp Gln Lys Gln Asn Glu
    305                 310                 315 cct ttt gtg gcc acc cag tca tct gcc tgc gtg gat ggc cct gca aac     1187
Pro Phe Val Ala Thr Gln Ser Ser Ala Cys Val Asp Gly Pro Ala Asn
320                 325                 330                 335 cat tgagcgtagg atttgttgca ttatgctaga gcaccaggg tcaggtgcaa            1240
His
```

-continued

```
ggaagaggct taagtatgtt cattttatc agaatgcaaa agcgaaaatt atgtcacttt      1300
aagaaatagc tactgtttgc aatgtcttat taaaaaacaa caaaaaaaga cacatggaac     1360
aaagaagctg tgaccccagc aggatgtcta atatgtgagg aaatgagatg tccacctaaa     1420
attcatatgt gacaaaatta tctcgacctt acataggagg agaatacttg aagcagtatg    1480
ctgctgtggt tagaagcaga ttttatactt ttaactggaa actttgggt ttgcatttag      1540 atcatttagc tgatggctaa atagcaaaat ttatatttag aagcaaaaaa aaaaagcata    1600
gagatgtgtt ttataaatag gtttatgtgt actggtttgc atgtacccac ccaaaatgat   1660
tatttttgga gaatctaagt caaactcact atttataatg cataggtaac cattaactat    1720
gtacatataa agtataaata tgtttatatt ctgtacatat ggtttaggtc accagatcct    1780
agtgtagttc tgaaactaag actatagata ttttgtttct tttgatttct ctttatacta    1840
aagaatccag agttgctaca ataaaataag gggaataata aaaaaaaaaa aaaa           1894
```

<210> SEQ ID NO 2
<211> LENGTH: 336
<212> TYPE: PRT
<213> ORGANISM: Homo sapiens
<220> FEATURE:
<223> OTHER INFORMATION: TWIK-1

<400> SEQUENCE: 2

```
Met Leu Gln Ser Leu Ala Gly Ser Ser Cys Val Arg Leu Val Glu Arg
  1               5                  10                  15

His Arg Ser Ala Trp Cys Phe Gly Phe Leu Val Leu Gly Tyr Leu Leu
             20                  25                  30

Tyr Leu Val Phe Gly Ala Val Val Phe Ser Ser Val Glu Leu Pro Tyr
         35                  40                  45

Glu Asp Leu Leu Arg Gln Glu Leu Arg Lys Leu Lys Arg Arg Phe Leu
     50                  55                  60

Glu Glu His Glu Cys Leu Ser Glu Gln Gln Leu Glu Gln Phe Leu Gly
 65                  70                  75                  80

Arg Val Leu Glu Ala Ser Asn Tyr Gly Val Ser Val Leu Ser Asn Ala
                 85                  90                  95

Ser Gly Asn Trp Asn Trp Asp Phe Thr Ser Ala Leu Phe Phe Ala Ser
            100                 105                 110

Thr Val Leu Ser Thr Thr Gly Tyr Gly His Thr Val Pro Leu Ser Asp
        115                 120                 125

Gly Gly Lys Ala Phe Cys Ile Ile Tyr Ser Val Ile Gly Ile Pro Phe
    130                 135                 140

Thr Leu Leu Phe Leu Thr Ala Val Val Gln Arg Ile Thr Val His Val
145                 150                 155                 160

Thr Arg Arg Pro Val Leu Tyr Phe His Ile Arg Trp Gly Phe Ser Lys
                165                 170                 175

Gln Val Val Ala Ile Val His Ala Val Leu Leu Gly Phe Val Thr Val
            180                 185                 190

Ser Cys Phe Phe Phe Ile Pro Ala Ala Val Phe Ser Val Leu Glu Asp
        195                 200                 205

Asp Trp Asn Phe Leu Glu Ser Phe Tyr Phe Cys Phe Ile Ser Leu Ser
    210                 215                 220

Thr Ile Gly Leu Gly Asp Tyr Val Pro Gly Glu Gly Tyr Asn Gln Lys
225                 230                 235                 240

Phe Arg Glu Leu Tyr Lys Ile Gly Ile Thr Cys Tyr Leu Leu Leu Gly
                245                 250                 255
```

```
Leu Ile Ala Met Leu Val Val Leu Glu Thr Phe Cys Glu Leu His Glu
            260                 265                 270

Leu Lys Lys Phe Arg Lys Met Phe Tyr Val Lys Lys Asp Lys Asp Glu
        275                 280                 285

Asp Gln Val His Ile Ile Glu His Asp Gln Leu Ser Phe Ser Ser Ile
        290                 295                 300

Thr Asp Gln Ala Ala Gly Met Lys Glu Asp Gln Lys Gln Asn Glu Pro
305                 310                 315                 320

Phe Val Ala Thr Gln Ser Ser Ala Cys Val Asp Gly Pro Ala Asn His
                325                 330                 335

<210> SEQ ID NO 3
<211> LENGTH: 2514
<212> TYPE: DNA
<213> ORGANISM: Homo sapiens
<220> FEATURE:
<221> NAME/KEY: CDS
<222> LOCATION: (126)..(1307)
<220> FEATURE:
<223> OTHER INFORMATION: TASK

<400> SEQUENCE: 3
tgccctgcgc ggatagcggc gagcgcagcc atgccccagg ccgcctccgg ggcagcagca      60
gcggcggccg gggccgatgc gcgggccggg ggcgccgggg ggcggcggc ggcccgggcg     120 ggacg atg aag cgg cag aac gtg cgc acg ctg gcg ctc atc gtg tgc acc    170
      Met Lys Arg Gln Asn Val Arg Thr Leu Ala Leu Ile Val Cys Thr
        1               5                  10                  15 ttc acc tac ctg ctg gtg ggc gcc gcg gtc ttc gac gcg ctg gag tcg    218
Phe Thr Tyr Leu Leu Val Gly Ala Ala Val Phe Asp Ala Leu Glu Ser
             20                  25                  30 gag ccc gag ctg atc gag cgg cag cgg ctg gag ctg cgg cag cag gag    266
Glu Pro Glu Leu Ile Glu Arg Gln Arg Leu Glu Leu Arg Gln Gln Glu
         35                  40                  45 ctg cgg gcg cgc tac aac ctc agc cag ggc ggc tac gag gag ctg gag    314
Leu Arg Ala Arg Tyr Asn Leu Ser Gln Gly Gly Tyr Glu Glu Leu Glu
     50                  55                  60 cgc gtc gtg ctg cgc ctc aag ccg cac aag gcc ggc gtg cag tgg cgc    362
Arg Val Val Leu Arg Leu Lys Pro His Lys Ala Gly Val Gln Trp Arg
 65                  70                  75 ttc gcc ggc tcc ttc tac ttc gcc atc acc gtc atc acc acc atc ggc    410
Phe Ala Gly Ser Phe Tyr Phe Ala Ile Thr Val Ile Thr Thr Ile Gly
 80                  85                  90                  95 tac ggg cac gcg gca ccc agc acg gat ggc ggc aag gtg ttc tgc atg    458
Tyr Gly His Ala Ala Pro Ser Thr Asp Gly Gly Lys Val Phe Cys Met
                100                 105                 110 ttc tac gcg ctg ctg ggc atc ccg ctc acg ctc gtc atg ttc cag agc    506
Phe Tyr Ala Leu Leu Gly Ile Pro Leu Thr Leu Val Met Phe Gln Ser
             115                 120                 125 ctg gga gag cgc atc aac acc ttg gtg agg tac ctg ctg cac cgc gcc    554
Leu Gly Glu Arg Ile Asn Thr Leu Val Arg Tyr Leu Leu His Arg Ala
         130                 135                 140 aag aag ggg ctg ggc atg cgg cgc gcc gac gtg tcc atg gcc aac atg    602
Lys Lys Gly Leu Gly Met Arg Arg Ala Asp Val Ser Met Ala Asn Met
     145                 150                 155 gtg ctc atc ggc ttc ttc tcg tgc atc agc acg ctg tgc atc ggc gcc    650
Val Leu Ile Gly Phe Phe Ser Cys Ile Ser Thr Leu Cys Ile Gly Ala
160                 165                 170                 175 gcc gcc ttc tcc cac tac gag cac tgg acc ttc ttc cag gcc tac tac    698
Ala Ala Phe Ser His Tyr Glu His Trp Thr Phe Phe Gln Ala Tyr Tyr
```

-continued

```
                    180                 185                 190
tac tgc ttc atc acc ctc acc acc atc ggc ttc ggc gac tac gtg gcg      746
Tyr Cys Phe Ile Thr Leu Thr Thr Ile Gly Phe Gly Asp Tyr Val Ala
            195                 200                 205 ctg cag aag gac cag gcc ctg cag acg cag ccg cag tac gtg gcc ttc      794
Leu Gln Lys Asp Gln Ala Leu Gln Thr Gln Pro Gln Tyr Val Ala Phe
            210                 215                 220 agc ttc gtc tac atc ctt acg ggc ctc acg gtc atc ggc gcc ttc ctc      842
Ser Phe Val Tyr Ile Leu Thr Gly Leu Thr Val Ile Gly Ala Phe Leu
            225                 230                 235 aac ctc gtg gtg ctg cgc ttc atg acc atg aac gcc gag gac gag aag      890
Asn Leu Val Val Leu Arg Phe Met Thr Met Asn Ala Glu Asp Glu Lys
240                 245                 250                 255 cgc gac gcc gag cac cgc gcg ctg ctc acg cgc aac ggg cag gcg ggc      938
Arg Asp Ala Glu His Arg Ala Leu Leu Thr Arg Asn Gly Gln Ala Gly
            260                 265                 270 ggc ggc gga ggg ggt ggc agc gcg cac act acg gac acc gcc tca tcc      986
Gly Gly Gly Gly Gly Gly Ser Ala His Thr Thr Asp Thr Ala Ser Ser
            275                 280                 285 acg gcg gca gcg ggc ggc ggc ggc ttc cgc aac gtc tac gcg gag gtg     1034
Thr Ala Ala Ala Gly Gly Gly Gly Phe Arg Asn Val Tyr Ala Glu Val
            290                 295                 300 ctg cac ttc cag tcc atg tgc tcg tgc ctg tgg tac aag agc cgc gag     1082
Leu His Phe Gln Ser Met Cys Ser Cys Leu Trp Tyr Lys Ser Arg Glu
            305                 310                 315 aag ctg cag tac tcc atc ccc atg atc atc ccg cgg gac ctc tcc acg     1130
Lys Leu Gln Tyr Ser Ile Pro Met Ile Ile Pro Arg Asp Leu Ser Thr
320                 325                 330                 335 tcc gac acg tgc gtg gag cag agc cac tcg tcg ccg gga ggg ggc ggc     1178
Ser Asp Thr Cys Val Glu Gln Ser His Ser Ser Pro Gly Gly Gly Gly
            340                 345                 350 cgc tac agc gac acg ccc tcg cga cgc tgc ctg tgc agc ggg gcg cca     1226
Arg Tyr Ser Asp Thr Pro Ser Arg Arg Cys Leu Cys Ser Gly Ala Pro
            355                 360                 365 cgc tcc gcc atc agc tcg gtg tcc acg ggt ctg cac agc ctg tcc acc     1274
Arg Ser Ala Ile Ser Ser Val Ser Thr Gly Leu His Ser Leu Ser Thr
            370                 375                 380 ttc cgc ggc ctc atg aag cgc agg agc tcc gtg tgactgcccc gagggacctg   1327
Phe Arg Gly Leu Met Lys Arg Arg Ser Ser Val
            385                 390 gagcacctgg gggcgcgggc gggggacccc tgctgggagg ccaggagact gcccctgctg   1387
ccttctgccc agtgggaccc cgcacaacat ccctcaccac tctcccccag cacccccatc   1447
tccgactgtg cctgcttgca ccagccggca ggaggccggg ctctgaggac ccctggggcc   1507
cccatcggag ccctgcaaat tccgagaaat gtgaaacttg gtggggtcag ggaggaaagg   1567
cagaagctgg gagcctccct tccctttgaa aatctaagaa gctcccagtc ctcagagacc   1627
ctgctggtac cacaccccac cttcggaggg gacttcatgt tccgtgtacg tttgcatctc   1687
tatttatacc tctgtcctgc taggtctccc accttccctt ggttccaaaa gccagggtgt   1747
ctatgtccaa gtcacccta ctcagcccca ctcccttcc tcatcccag ctgtgtctcc       1807 caacctccct tcgtgttgtt ttgcatggct ttgcagttat ggagaaagtg gaaacccagc   1867
agtccctaaa gctggtcccc agaaagcagg acagaaagaa ggagggacag gcaggcagca   1927
ggaggggcga gctgggaggc aggaggcagc ggcctgtcag tctgcagaat ggtcgcactg   1987
gaggttcaag ctaactggcc tccagccaca ttctcatagc aggtaggact tcagccttcc   2047
agacactgcc cttagaatct ggaacagaag acttcagact caccataatt gctgataatt   2107
```

```
acccactctt aaatttgtcg agtgattttt agcctctgaa aactctatgc tggccactga    2167
ttcctttgag tctcacaaaa ccctacttag gtcatcaggg caggagttct cactcccatt    2227
ttacagatga acctgtattc ccaacacttt tggaggctga ggttggagga ttgcttgagc    2287
ccaggaattc gagaccagcc taggtgacat agtgagaccc catctctaca aaaaataaaa    2347
aattaaccag gtgtggtggc acgtgcctgg gagtcccagc gacttgggag gctgaggtgg    2407
gaggattgtt tgagcctggg aggtcgaggc tgtagtgagc cctgattgca ccactgtact    2467
ccagcctggg tgacagggca agaccctgtc tcaaaaaaaa aaaaaaa                  2514

<210> SEQ ID NO 4
<211> LENGTH: 394
<212> TYPE: PRT
<213> ORGANISM: Homo sapiens
<220> FEATURE:
<223> OTHER INFORMATION: TASK

<400> SEQUENCE: 4

Met Lys Arg Gln Asn Val Arg Thr Leu Ala Leu Ile Val Cys Thr Phe
  1               5                  10                  15

Thr Tyr Leu Leu Val Gly Ala Ala Val Phe Asp Ala Leu Glu Ser Glu
                 20                  25                  30

Pro Glu Leu Ile Glu Arg Gln Arg Leu Glu Leu Arg Gln Gln Glu Leu
             35                  40                  45

Arg Ala Arg Tyr Asn Leu Ser Gln Gly Gly Tyr Glu Glu Leu Glu Arg
         50                  55                  60

Val Val Leu Arg Leu Lys Pro His Lys Ala Gly Val Gln Trp Arg Phe
 65                  70                  75                  80

Ala Gly Ser Phe Tyr Phe Ala Ile Thr Val Ile Thr Thr Ile Gly Tyr
                 85                  90                  95

Gly His Ala Ala Pro Ser Thr Asp Gly Gly Lys Val Phe Cys Met Phe
            100                 105                 110

Tyr Ala Leu Leu Gly Ile Pro Leu Thr Leu Val Met Phe Gln Ser Leu
        115                 120                 125

Gly Glu Arg Ile Asn Thr Leu Val Arg Tyr Leu Leu His Arg Ala Lys
    130                 135                 140

Lys Gly Leu Gly Met Arg Arg Ala Asp Val Ser Met Ala Asn Met Val
145                 150                 155                 160

Leu Ile Gly Phe Phe Ser Cys Ile Ser Thr Leu Cys Ile Gly Ala Ala
                165                 170                 175

Ala Phe Ser His Tyr Glu His Trp Thr Phe Phe Gln Ala Tyr Tyr Tyr
            180                 185                 190

Cys Phe Ile Thr Leu Thr Thr Ile Gly Phe Gly Asp Tyr Val Ala Leu
        195                 200                 205

Gln Lys Asp Gln Ala Leu Gln Thr Gln Pro Gln Tyr Val Ala Phe Ser
    210                 215                 220

Phe Val Tyr Ile Leu Thr Gly Leu Thr Val Ile Gly Ala Phe Leu Asn
225                 230                 235                 240

Leu Val Val Leu Arg Phe Met Thr Met Asn Ala Glu Asp Glu Lys Arg
                245                 250                 255

Asp Ala Glu His Arg Ala Leu Leu Thr Arg Asn Gly Gln Ala Gly Gly
            260                 265                 270

Gly Gly Gly Gly Gly Ser Ala His Thr Thr Asp Thr Ala Ser Ser Thr
        275                 280                 285
```

```
Ala Ala Ala Gly Gly Gly Gly Phe Arg Asn Val Tyr Ala Glu Val Leu
        290             295                 300

His Phe Gln Ser Met Cys Ser Cys Leu Trp Tyr Lys Ser Arg Glu Lys
305             310                 315                 320

Leu Gln Tyr Ser Ile Pro Met Ile Ile Pro Arg Asp Leu Ser Thr Ser
                325                 330                 335

Asp Thr Cys Val Glu Gln Ser His Ser Ser Pro Gly Gly Gly Gly Arg
            340                 345                 350

Tyr Ser Asp Thr Pro Ser Arg Arg Cys Leu Cys Ser Gly Ala Pro Arg
        355                 360                 365

Ser Ala Ile Ser Ser Val Ser Thr Gly Leu His Ser Leu Ser Thr Phe
    370                 375                 380

Arg Gly Leu Met Lys Arg Arg Ser Ser Val
385                 390

<210> SEQ ID NO 5
<211> LENGTH: 405
<212> TYPE: PRT
<213> ORGANISM: Murine
<220> FEATURE:
<223> OTHER INFORMATION: TASK

<400> SEQUENCE: 5

Glu Asn Val Arg Thr Leu Ala Leu Ile Val Cys Thr Phe Thr Tyr Leu
  1               5                  10                  15

Leu Val Gly Ala Ala Val Phe Asp Ala Leu Glu Ser Glu Pro Glu Met
              20                  25                  30

Ile Glu Arg Gln Arg Leu Glu Leu Arg Gln Leu Glu Leu Arg Ala Arg
          35                  40                  45

Tyr Asn Leu Ser Glu Gly Gly Tyr Glu Glu Leu Glu Arg Val Val Leu
     50                  55                  60

Arg Leu Lys Pro His Lys Ala Gly Val Gln Trp Arg Phe Ala Gly Ser
 65                  70                  75                  80

Phe Tyr Phe Ala Ile Thr Val Ile Thr Thr Ile Gly Tyr Gly His Ala
              85                  90                  95

Ala Pro Ser Thr Asp Gly Gly Lys Val Phe Cys Met Phe Tyr Ala Leu
         100                 105                 110

Leu Gly Ile Pro Leu Thr Leu Ile Met Phe Gln Ser Leu Gly Glu Arg
     115                 120                 125

Ile Asn Thr Phe Val Arg Tyr Leu Leu His Arg Ala Lys Arg Gly Leu
130                 135                 140

Gly Met Arg His Ala Glu Val Ser Met Ala Asn Met Val Leu Ile Gly
145                 150                 155                 160

Phe Val Ser Cys Ile Ser Thr Leu Cys Ile Gly Ala Ala Ala Phe Ser
              165                 170                 175

Tyr Tyr Glu Arg Trp Thr Phe Phe Gln Ala Tyr Tyr Tyr Cys Phe Ile
          180                 185                 190

Thr Leu Thr Thr Ile Gly Phe Gly Asp Tyr Val Ala Leu Gln Lys Asp
     195                 200                 205

Gln Ala Leu Gln Thr Gln Pro Gln Tyr Val Ala Phe Ser Phe Val Tyr
210                 215                 220

Ile Leu Thr Gly Leu Thr Val Ile Gly Ala Phe Leu Asn Leu Val Val
225                 230                 235                 240

Leu Arg Phe Met Thr Met Asn Ala Glu Asp Glu Lys Arg Asp Ala Glu
              245                 250                 255
```

His Arg Ala Leu Leu Thr His Asn Gly Gln Ala Val Gly Leu Gly Gly
            260                 265                 270

Leu Ser Cys Leu Ser Gly Ser Leu Gly Asp Val Arg Pro Arg Asp Pro
            275                 280                 285

Val Thr Cys Ala Ala Ala Gly Gly Val Gly Val Gly Val Gly Gly
            290                 295                 300

Ser Gly Phe Arg Asn Val Tyr Ala Glu Val Leu His Phe Gln Ser Met
305                 310                 315                 320

Cys Ser Cys Leu Trp Tyr Lys Ser Arg Glu Lys Leu Gln Tyr Ser Ile
            325                 330                 335

Pro Met Ile Ile Pro Arg Asp Leu Ser Thr Ser Asp Thr Cys Val Glu
            340                 345                 350

His Ser His Ser Ser Pro Gly Gly Gly Arg Tyr Ser Asp Thr Pro
            355                 360                 365

Ser His Pro Cys Leu Cys Ser Gly Thr Gln Arg Ser Ala Ile Ser Ser
            370                 375                 380

Val Ser Thr Gly Leu His Ser Leu Ala Ala Phe Arg Gly Leu Met Lys
385                 390                 395                 400

Arg Arg Ser Ser Val
            405

<210> SEQ ID NO 6
<211> LENGTH: 347
<212> TYPE: PRT
<213> ORGANISM: Unknown
<220> FEATURE:
<223> OTHER INFORMATION: Description of Unknown Organism: TWIK-1 homolog

<400> SEQUENCE: 6

Met Tyr Thr Asp Glu Gly Glu Tyr Ser Gly Asp Thr Asp His Gly Gly
 1               5                  10                  15

Ser Thr Met Gln Lys Met Ser Pro Asn Thr Arg Gln Asn Phe Arg Gln
            20                  25                  30

Asn Val Asn Val Val Cys Leu Ser Ala Ala Ile Thr Leu Leu Val
            35                  40                  45

Phe Asn Leu Ile Gly Ala Gly Ile Phe Tyr Leu Ala Glu Thr Gln Asn
     50                  55                  60

Ser Ser Glu Ser Leu Asn Glu Asn Ser Glu Val Ser Lys Cys Leu His
65                  70                  75                  80

Asn Leu Pro Ile Gly Gly Lys Ile Thr Ala Glu Met Lys Ser Lys Leu
            85                  90                  95

Gly Lys Cys Leu Thr Lys Ser Ser Arg Ile Asp Gly Phe Gly Lys Ala
            100                 105                 110

Ile Phe Phe Ser Trp Thr Leu Tyr Ser Thr Val Gly Tyr Gly Ser Leu
            115                 120                 125

Tyr Pro His Ser Thr Leu Gly Arg Tyr Leu Thr Ile Phe Tyr Ser Leu
            130                 135                 140

Leu Met Ile Pro Val Phe Ile Ala Phe Lys Phe Glu Phe Gly Thr Phe
145                 150                 155                 160

Leu Ala His Phe Leu Val Val Ser Asn Arg Thr Arg Leu Ala Val
            165                 170                 175

Lys Lys Ala Tyr Tyr Lys Leu Ser Gln Asn Pro Glu Asn Ala Glu Thr
            180                 185                 190

Pro Ser Asn Ser Leu Gln His Asp Tyr Leu Ile Phe Leu Ser Ser Leu
            195                 200                 205

```
Leu Leu Cys Ser Ile Ser Leu Ser Ser Ala Leu Phe Ser Ser
        210             215             220

Ile Glu Asn Ile Ser Tyr Leu Ser Ser Val Tyr Phe Gly Ile Thr
225             230             235             240

Met Phe Leu Ile Gly Ile Gly Asp Ile Val Pro Thr Asn Leu Val Trp
                245             250             255

Phe Ser Gly Tyr Cys Met Leu Phe Leu Ile Ser Asp Val Leu Ser Asn
            260             265             270

Gln Ile Phe Tyr Phe Cys Gln Ala Arg Val Arg Tyr Phe Phe His Ile
            275             280             285

Leu Ala Arg Lys Ile Leu Leu Arg Glu Glu Asp Gly Phe Gln
        290             295             300

Leu Glu Thr Thr Val Ser Leu Gln His Ile Pro Ile Ile Asn Ser Gln
305             310             315             320

Cys Met Pro Ser Leu Val Leu Asp Cys Glu Lys Glu Leu Asp Asn
                325             330             335

Asp Glu Lys Leu Ile Ser Ser Leu Thr Ser Thr
            340             345
```

<210> SEQ ID NO 7
<211> LENGTH: 383
<212> TYPE: PRT
<213> ORGANISM: Unknown
<220> FEATURE:
<223> OTHER INFORMATION: Description of Unknown Organism: TWIK-1 homolog

<400> SEQUENCE: 7

```
Met Thr Val Ser Met Glu Glu Asn Ser Lys Ile Gln Met Leu Ser Ala
 1               5                  10                  15

Thr Ser Lys Asp Lys Val Ala Thr Asp Arg Ser Leu Leu Asn Lys
            20              25                  30

Tyr His Leu Gly Pro Leu Ala Leu His Thr Gly Leu Val Leu Ser Cys
        35              40                  45

Val Thr Tyr Ala Leu Gly Gly Ala Tyr Leu Phe Leu Ser Ile Glu His
    50              55                  60

Pro Glu Glu Leu Lys Arg Arg Glu Lys Ala Ile Arg Glu Phe Gln Asp
65              70              75                  80

Leu Lys Gln Gln Phe Met Gly Asn Ile Thr Ser Gly Ile Glu Asn Ser
                85              90                  95

Glu Gln Ser Ile Glu Ile Tyr Thr Lys Lys Leu Ile Leu Met Leu Glu
            100             105                 110

Asp Ala His Asn Ala His Ala Phe Glu Tyr Phe Phe Leu Asn His Glu
        115             120                 125

Ile Pro Lys Asp Met Trp Thr Phe Ser Ser Ala Leu Val Phe Thr Thr
    130             135                 140

Thr Thr Val Ile Pro Val Gly Tyr Gly Tyr Ile Phe Pro Val Ser Ala
145             150             155                 160

Tyr Gly Arg Met Cys Leu Ile Ala Tyr Ala Leu Leu Gly Ile Pro Leu
                165             170                 175

Thr Leu Val Thr Met Ala Asp Thr Gly Lys Phe Ala Ala Gln Leu Val
            180             185                 190

Thr Arg Trp Phe Gly Asp Asn Asn Met Ala Ile Pro Ala Ala Ile Phe
        195             200                 205

Val Cys Leu Leu Phe Ala Tyr Pro Leu Val Val Gly Phe Ile Leu Cys
    210             215                 220
```

```
Ser Thr Ser Asn Ile Thr Tyr Leu Asp Ser Val Tyr Phe Ser Leu Thr
225                 230                 235                 240

Ser Ile Phe Thr Ile Gly Phe Gly Asp Leu Thr Pro Asp Met Asn Val
                245                 250                 255

Ile His Met Val Leu Phe Leu Ala Val Gly Val Ile Leu Val Thr Ile
                260                 265                 270

Thr Leu Asp Ile Val Ala Ala Glu Met Ile Asp Arg Val His Tyr Met
            275                 280                 285

Gly Arg His Val Gly Lys Ala Lys Glu Leu Ala Gly Lys Met Phe Gln
        290                 295                 300

Leu Ala Gln Ser Leu Asn Met Lys Gln Gly Leu Val Ser Gly Val Gly
305                 310                 315                 320

Gln Leu His Ala Leu Ala Arg Phe Gly Met Leu Val Gly Arg Glu Glu
                325                 330                 335

Val Asp Lys Thr Gln Glu Asp Gly Ile Ile Ala Phe Ser Pro Asp Val
                340                 345                 350

Met Asp Gly Leu Glu Phe Met Asp Thr Leu Ser Ile Tyr Ser Arg Arg
            355                 360                 365

Ser Arg Arg Ser Ala Glu Asn Ser Ala Arg Asn Leu Phe Leu Ser
370                 375                 380

<210> SEQ ID NO 8
<211> LENGTH: 370
<212> TYPE: PRT
<213> ORGANISM: Murine
<220> FEATURE:
<223> OTHER INFORMATION: TREK-1

<400> SEQUENCE: 8

Met Ala Ala Pro Asp Leu Leu Asp Pro Lys Ser Ala Ala Gln Asn Ser
1               5                   10                  15

Lys Pro Arg Leu Ser Phe Ser Ser Lys Pro Thr Val Leu Ala Ser Arg
                20                  25                  30

Val Glu Ser Asp Ser Ala Ile Asn Val Met Lys Trp Lys Thr Val Ser
            35                  40                  45

Thr Ile Phe Leu Val Val Val Leu Tyr Leu Ile Ile Gly Ala Ala Val
        50                  55                  60

Phe Lys Ala Leu Glu Gln Pro Gln Glu Ile Ser Gln Arg Thr Thr Ile
65                  70                  75                  80

Val Ile Gln Lys Gln Thr Phe Ile Ala Gln His Ala Cys Val Asn Ser
                85                  90                  95

Thr Glu Leu Asp Glu Leu Ile Gln Gln Ile Val Ala Ala Ile Asn Ala
            100                 105                 110

Gly Ile Ile Pro Leu Gly Asn Ser Ser Asn Gln Val Ser His Trp Asp
        115                 120                 125

Leu Gly Ser Ser Phe Phe Ala Gly Thr Val Ile Thr Thr Ile Gly
130                 135                 140

Phe Gly Asn Ile Ser Pro Arg Thr Glu Gly Gly Lys Ile Phe Cys Ile
145                 150                 155                 160

Ile Tyr Ala Leu Leu Gly Ile Pro Leu Glu Gly Phe Leu Leu Ala Gly
                165                 170                 175

Val Gly Asp Gln Leu Gly Thr Ile Phe Gly Lys Gly Ile Ala Lys Val
            180                 185                 190

Glu Asp Thr Phe Ile Lys Trp Asn Val Ser Gln Thr Lys Ile Arg Ile
        195                 200                 205
```

```
Ile Ser Thr Ile Ile Phe Ile Leu Phe Gly Cys Val Leu Phe Val Ala
    210                 215                 220

Leu Pro Ala Val Ile Phe Lys His Ile Glu Gly Trp Ser Ala Leu Asp
225                 230                 235                 240

Ala Ile Tyr Phe Val Val Ile Thr Leu Thr Thr Ile Gly Phe Gly Asp
                245                 250                 255

Tyr Val Ala Gly Gly Ser Asp Ile Glu Tyr Leu Asp Phe Tyr Lys Pro
                260                 265                 270

Val Val Trp Phe Trp Ile Leu Val Gly Leu Ala Tyr Phe Ala Ala Val
            275                 280                 285

Leu Ser Met Ile Gly Asp Trp Leu Arg Val Ile Ser Lys Lys Thr Lys
    290                 295                 300

Glu Glu Val Gly Glu Phe Arg Ala His Ala Ala Glu Trp Thr Ala Asn
305                 310                 315                 320

Val Thr Ala Glu Phe Lys Glu Thr Arg Arg Leu Ser Val Glu Ile
                325                 330                 335

Tyr Asp Lys Phe Gln Arg Ala Thr Ser Val Lys Arg Lys Leu Ser Ala
                340                 345                 350

Glu Leu Ala Gly Asn His Asn Gln Glu Leu Thr Pro Cys Met Arg Thr
            355                 360                 365

Cys Leu
    370

<210> SEQ ID NO 9
<211> LENGTH: 27
<212> TYPE: PRT
<213> ORGANISM: Homo sapiens
<220> FEATURE:
<223> OTHER INFORMATION: TWIK-1 P1

<400> SEQUENCE: 9

Phe Thr Ser Ala Leu Phe Phe Ala Ser Thr Val Leu Ser Thr Thr Gly
1               5                   10                  15

Tyr Gly His Thr Val Pro Leu Ser Asp Gly Gly
            20                  25

<210> SEQ ID NO 10
<211> LENGTH: 27
<212> TYPE: PRT
<213> ORGANISM: Homo sapiens
<220> FEATURE:
<223> OTHER INFORMATION: TWIK-1 P2

<400> SEQUENCE: 10

Phe Leu Glu Ser Phe Tyr Phe Cys Phe Ile Ser Leu Ser Thr Ile Gly
1               5                   10                  15

Leu Gly Asp Tyr Val Pro Gly Glu Gly Tyr Asn
            20                  25

<210> SEQ ID NO 11
<211> LENGTH: 27
<212> TYPE: PRT
<213> ORGANISM: Unknown
<220> FEATURE:
<223> OTHER INFORMATION: Description of Unknown Organism: P domain of
      representative K+ channel sequence
<220> FEATURE:
<223> OTHER INFORMATION: TOK-1 P2

<400> SEQUENCE: 11

Tyr Phe Asn Cys Ile Tyr Phe Cys Phe Leu Cys Leu Leu Thr Ile Gly
```

```
                1               5              10              15

Tyr Gly Asp Tyr Ala Pro Arg Thr Gly Ala Gly
               20              25

<210> SEQ ID NO 12
<211> LENGTH: 27
<212> TYPE: PRT
<213> ORGANISM: Unknown
<220> FEATURE:
<223> OTHER INFORMATION: Description of Unknown Organism: P domain of
      representative K+ channel sequence
<220> FEATURE:
<223> OTHER INFORMATION: TOK-1 P1

<400> SEQUENCE: 12

Tyr Gly Asn Ala Leu Tyr Phe Cys Thr Val Ser Leu Leu Thr Val Gly
  1               5              10              15

Leu Gly Asp Ile Leu Pro Lys Ser Val Gly Ala
               20              25

<210> SEQ ID NO 13
<211> LENGTH: 27
<212> TYPE: PRT
<213> ORGANISM: Unknown
<220> FEATURE:
<223> OTHER INFORMATION: Description of Unknown Organism: P domain of
      representative K+ channel sequence
<220> FEATURE:
<223> OTHER INFORMATION: Slo

<400> SEQUENCE: 13

Tyr Trp Thr Cys Val Tyr Phe Leu Ile Val Thr Met Ser Thr Val Gly
  1               5              10              15

Tyr Gly Asp Val Tyr Cys Glu Thr Val Leu Gly
               20              25

<210> SEQ ID NO 14
<211> LENGTH: 27
<212> TYPE: PRT
<213> ORGANISM: Unknown
<220> FEATURE:
<223> OTHER INFORMATION: Description of Unknown Organism: P domain of
      representative K+ channel sequence
<220> FEATURE:
<223> OTHER INFORMATION: Shaker

<400> SEQUENCE: 14

Ile Pro Asp Ala Phe Trp Trp Ala Val Val Thr Met Thr Thr Val Gly
  1               5              10              15

Tyr Gly Asp Met Thr Pro Val Gly Phe Trp Gly
               20              25

<210> SEQ ID NO 15
<211> LENGTH: 27
<212> TYPE: PRT
<213> ORGANISM: Unknown
<220> FEATURE:
<223> OTHER INFORMATION: Description of Unknown Organism: P domain of
      representative K+ channel sequence
<220> FEATURE:
<223> OTHER INFORMATION: Shab

<400> SEQUENCE: 15

Ile Pro Glu Ala Phe Trp Trp Ala Gly Ile Thr Met Thr Thr Val Gly
  1               5              10              15

Tyr Gly Asp Ile Cys Pro Thr Thr Ala Leu Gly
```

-continued

<210> SEQ ID NO 16
<211> LENGTH: 27
<212> TYPE: PRT
<213> ORGANISM: Unknown
<220> FEATURE:
<223> OTHER INFORMATION: Description of Unknown Organism: P domain of
      representative K+ channel sequence
<220> FEATURE:
<223> OTHER INFORMATION: Shal

<400> SEQUENCE: 16

Ile Pro Ala Ala Phe Trp Tyr Thr Ile Val Thr Met Thr Thr Leu Gly
 1               5                  10                  15

Tyr Gly Asp Met Val Pro Glu Thr Ile Ala Gly
            20                  25

<210> SEQ ID NO 17
<211> LENGTH: 27
<212> TYPE: PRT
<213> ORGANISM: Unknown
<220> FEATURE:
<223> OTHER INFORMATION: Description of Unknown Organism: P domain of
      representative K+ channel sequence
<220> FEATURE:
<223> OTHER INFORMATION: Shaw

<400> SEQUENCE: 17

Ile Pro Leu Gly Leu Trp Trp Ala Leu Val Thr Met Thr Thr Val Gly
 1               5                  10                  15

Tyr Gly Asp Met Ala Pro Lys Thr Tyr Ile Gly
            20                  25

<210> SEQ ID NO 18
<211> LENGTH: 27
<212> TYPE: PRT
<213> ORGANISM: Unknown
<220> FEATURE:
<223> OTHER INFORMATION: Description of Unknown Organism: P domain of
      representative K+ channel sequence
<220> FEATURE:
<223> OTHER INFORMATION: KAT1

<400> SEQUENCE: 18

Tyr Val Thr Ala Leu Tyr Trp Ser Ile Thr Thr Leu Thr Thr Thr Gly
 1               5                  10                  15

Tyr Gly Asp Phe His Ala Glu Asn Pro Arg Glu
            20                  25

<210> SEQ ID NO 19
<211> LENGTH: 27
<212> TYPE: PRT
<213> ORGANISM: Unknown
<220> FEATURE:
<223> OTHER INFORMATION: Description of Unknown Organism: P domain of
      representative K+ channel sequence
<220> FEATURE:
<223> OTHER INFORMATION: AKT1

<400> SEQUENCE: 19

Tyr Val Thr Ser Met Tyr Trp Ser Ile Thr Thr Leu Thr Thr Val Gly
 1               5                  10                  15

Tyr Gly Asp Ile His Pro Val Asn Thr Lys Glu
            20                  25

```
<210> SEQ ID NO 20
<211> LENGTH: 27
<212> TYPE: PRT
<213> ORGANISM: Unknown
<220> FEATURE:
<223> OTHER INFORMATION: Description of Unknown Organism: P domain of
      representative K+ channel sequence
<220> FEATURE:
<223> OTHER INFORMATION: eag

<400> SEQUENCE: 20

Tyr Val Thr Ala Leu Tyr Phe Thr Met Thr Cys Met Thr Ser Val Gly
  1               5                  10                  15

Phe Gly Asn Val Ala Ala Glu Thr Asp Asn Glu
             20                  25

<210> SEQ ID NO 21
<211> LENGTH: 27
<212> TYPE: PRT
<213> ORGANISM: Unknown
<220> FEATURE:
<223> OTHER INFORMATION: Description of Unknown Organism: P domain of
      representative K+ channel sequence
<220> FEATURE:
<223> OTHER INFORMATION: ROMK1

<400> SEQUENCE: 21

Met Thr Ser Ala Phe Leu Phe Ser Leu Glu Thr Gln Val Thr Ile Gly
  1               5                  10                  15

Tyr Gly Phe Arg Phe Val Thr Glu Gln Cys Ala
             20                  25

<210> SEQ ID NO 22
<211> LENGTH: 27
<212> TYPE: PRT
<213> ORGANISM: Unknown
<220> FEATURE:
<223> OTHER INFORMATION: Description of Unknown Organism: P domain of
      representative K+ channel sequence
<220> FEATURE:
<223> OTHER INFORMATION: IRK1

<400> SEQUENCE: 22

Phe Thr Ala Ala Phe Leu Phe Ser Ile Glu Thr Gln Thr Thr Ile Gly
  1               5                  10                  15

Tyr Gly Phe Arg Cys Val Thr Asp Glu Cys Pro
             20                  25

<210> SEQ ID NO 23
<211> LENGTH: 27
<212> TYPE: PRT
<213> ORGANISM: Unknown
<220> FEATURE:
<223> OTHER INFORMATION: Description of Unknown Organism: P domain of
      representative K+ channel sequence
<220> FEATURE:
<223> OTHER INFORMATION: GIRK1

<400> SEQUENCE: 23

Phe Pro Ser Ala Phe Leu Phe Phe Ile Glu Thr Glu Ala Thr Ile Gly
  1               5                  10                  15

Tyr Gly Tyr Arg Tyr Ile Thr Asp Lys Cys Pro
             20                  25

<210> SEQ ID NO 24
<211> LENGTH: 48
<212> TYPE: DNA
```

```
<213> ORGANISM: Artificial Sequence
<220> FEATURE:
<223> OTHER INFORMATION: Description of Artificial Sequence: antisense
      oligonucleotide complementary to the partial
      mouse cDNA sequence of TASK

<400> SEQUENCE: 24
caccagcagg taggtgaagg tgcacacgat gagagccaac gtgcgcac                    48
```

All references cited in this text are expressly incorporated herein by reference.

REFERENCES

Altschul, S. F., Gich, W., Miller, W., Myers, E. W. and Lipman, D. J. (1990) Basic local alignment search tool. *J. MoL Biol.*, 215, 403–410.

Backx, P. H. and Marban, E. (1993) Background potassium current active during the plateau of the action potential in Guinea-pig ventricular myocytes. *Circulation Res.*, 72, 890–900.

Barhanin, J., Lesage, F., Guillemare, E., Fink, M., Lazdunski, M. and Romey, G. (1996) KvLQT1 and IsK (minK) proteins associate to form the IKs cardiac potassium current. *Nature.*, 384, 78–80.

Borgula, G. A., Karwoski, C. J. and Steinberg, R. H. (1989) Light-evoked changes in extracellular pH in frog retina. *Vision Res.*, 29, 1069–1077.

Buckler, K. J. (1997) A novel oxygen-sensitive potassium current in rat carotid body type I cells. *J. Physiol. (London).*, 498, 649–662.

Chesler, M. (1990) The regulation and modulation of pH in the nervous system. *Prog Neurobiol.*, 34, 401–427.

Chesler, M. and Kaila, K. (1992) Modulation of pH by neuronal activity. *Trends Neurosci.*, 15, 386–402.

Doupnik, C. A., Davidson, N. and Lester, H. A. (1995) The inward rectifier potassium channel family. *Curr. Opin. Neurobiol.*, 5, 268–277.

Fakler, B. and Ruppersberg, J. P. (1996) Functional and molecular diversity classifies the family of inward-rectifier $K^+$ channels. *Cell. Physiol. Biochem.*, 6, 195–209.

Fink, M., Duprat, F., Lesage, F., Heurteaux, C., Romey, G., Barhanin, J. and Lazdunski, M. (1996a) A new $K^+$ channel β subunit to specifically enhance Kv2.2 (CDRK) expression. *J Biol. Chem.*, 271, 26341–26348.

Fink, M., Duprat, F., Lesage, F., Reyes, R., Romey, G., Heurteaux, C. and Lazdunski, M. (1996b) Cloning, functional expression and brain localization of a novel unconventional outward rectifier $K^+$ channel. *EMBO J.*, 15, 6854–6862.

Goldstein, S. A. N., Price, L. A., Rosenthal, D. N. and Pausch, M. H. (1996) ORK1, a potassium-selective leak channel with two pore domains cloned from *Drosophila melanogaster* by expression in *Saccharomyces cerevisiae*. *Proc. Natl. Acad Sci. USA.*, 93, 13256–13261.

Guillemare, E., Honore, E., Pradier, L., Lesage, F., Schweitz, H., Attali, B., Barhanin, J. and Lazdunski, M. (1992) Effects of the level of messenger RNA expression on biophysical properties, sensitivity to neurotoxins, and regulation of the brain delayed-rectifier $K^+$ channel Kvl.2. *Biochemistry.*, 31, 12463–12468.

Heginbotham, L., Lu, Z., Abramson, T. and Mackinnon, R. (1994) Mutations in the $K^+$ channel signature sequence. *Biophys. J*, 66, 1061–1067.

Hille, B. (1992) in (ed.) *Ionic channels of excitable membranes.* Sinauer Associates Inc., Sunderland, Mass., pp. 1–607.

Inagaki, N., Gonoi, T., Clement, J. P., Wang, C. Z., Aguilarbryan, L., Bryan, J. and Seino, S. (1996) A family of sulfonylurea receptors determines the pharmacological properties of ATP-sensitive $K^+$ channels. *Neuron.*, 16, 1011–1017.

Jan, L. Y. and Jan, Y. N. (1994) Potassium channels and their evolving gates. *Nature.*, 371, 119–122.

Jurman, M. E., Boland, L. M. and Yellen, G. (1994) Visual identification of individual transfected cells for electrophysiology using antibody-coated beads. *BioTechniques.*, 17, 876–881.

Knaus, H. G., Folander, K., Garciacalvo, M., Garcia, M. L., Kaczorowski, G. J., Smith, M. and Swanson, R. (1994) Primary sequence and immunological characterization of beta-subunit of high conductance $Ca^{2+}$-activated $K^+$ channel from smooth muscle. *J Biol. Chem.*, 269, 17274–17278.

Kohler, M., Hirschberg, B., Bond, C. T., Kinzie, J. M., Marrion, N. V., Maylie, J. and Adelman, J. P. (1996) Small-conductance, calcium-activated potassium channels from mammalian brain. *Science.*, 273, 1709–1714.

Koyano, K., Tanaka, K. and Kuba, K. (1992) A patch-clamp study on the muscarine-sensitive potassium channel in bullfrog sympathetic ganglion cells. *J PhysioL (London).*, 454, 231–246.

Kraig, R. P., Ferreira-Filho, C. R. and Nicholson, C. (1983) Alkaline and acid transients in cerebellar microenvironment. *J Neurophysiol.*, 49, 831–851.

Krishtal, O. A., Osipchuk, Y. V., Shelest, T. N. and Smimoff, S. V. (1987) Rapid extracellular Ph transients related to synaptic transmission in rat hippocampal slices. *Brain Res.*, 436, 352–356.

Kyte, J. and Doolittle, R. (1982) A simple model for displaying the hydropathic character of a protein. *J MoL Biol.*, 157, 105–106.

Lesage, F., Attali, B., Lazdunski, M. and Barhanin, J. (1992) Developmental expression of voltage-sensitive $K^+$ channels in mouse skeletal muscle and C2C12 cells. *FEBS Lett.*, 310, 162–166.

Lesage, F., Guillemare, E., Fink, M., Duprat, F., Heurteaux, C., Fosset, M., Romey, G., Barhanin, J. and Lazdunski, M. (1995) Molecular properties of neuronal G-protein-activated inwardly rectifying $K^+$ channels. *J. Biol. Chem.*, 270, 28660–28667.

Lesage, F., Guillemare, E., Fink, M., Duprat, F., Lazdunski, M., Romey, G. and Barhanin, J. (1996a) TWIK-1, a ubiquitous human weakly inward rectifying $K^+$ channel with a novel structure. *EMBO J.*, 15, 1004–1011.

Lesage, F., Lauritzen, I., Duprat, F., Reyes, R., Fink, M., Heurteaux, C. and Lazdunski, M. (1997) The structure, finction and distribution of the mouse TWIK-1 $K^+$ channels. *FEBS Lett.*, 402, 28–32.

Lesage, F., Reyes, R., Fink, M., Duprat, F., Guillemare, E. and Lazdunski, M. (1996b) Dimerization of TWIK-1 K$^+$ channel subunits via a disulfide bridge. *EMBO J.*, 15, 6400–6407.

Lingueglia, E., Voilley, N., Waldmann, R., Lazdunski, M. and Barbry, P. (1993) Expression cloning of an epithelial amiloride-sensitive Na$^+$ channel. A new channel type with homologies to *Caenorhabditis elegans* degenerins. *FEBS Lett.*, 318, 95–99.

MacCobb, D. P., Fowler, N. L., Featherstone, T., Lingle, C. J., Saito, M., Krause, J. E. and Salkoff, L. (1995) A human calcium-activated potassium channel gene expressed in vascular smooth muscle. *Am. J Physiol. -Heart Circ. Physiol.*, 38, H767–H777.

MacManus, O. B., Helms, L. M. H., Pallanck, L., Ganetzld, B., Swanson, R. and Leonard, R. J. (1995) *Neuron.*, 15, 645–650.

Mutch, W. A. C. and Hansen, A. J. (1984) Extracellular pH changes during depression and cerebral ischemia: mechanisms of brain pH regulation. *J. Cereb. Blood Flow Metab.*, 4, 17–27.

Nedergaard, M., Kraig, R. P., Tanabe, J. and Pulsinelli, W. A. (1991) Dynamics of interstitial and intracellular pH in evolving brain infarct. *Am. J. Physiol.*, 260, R581–R588.

Pongs, O. (1992) Molecular biology of voltage-dependent potassium channels. *Physiol. Rev.*, 72, S69–S88.

Pongs, O. (1995) Regulation of the activity of voltage-gated potassium channels by beta subunits. *Semin. Neurosci.*, 7, 137–146.

Rudy, B. (1988) Diversity and ubiquity of K$^+$ channels. *Neuroscience.*, 25, 729–749.

Sanguinetti, M. C., Curran, M. E., Zou, A., Shen, J., Spector, P. S., Atkinson, D. L. and Keating, M. T. (1996) Coassembly of KvLQT1 and MinK (IsK) proteins to form cardiac I$_{KS}$ potassium channel. *Nature.*, 384, 80–83.

Shen, K. Z., North, R. A. and Surprenant, A. (1992) Potassium channels opened by noradrenaline and other transmitters in excised membrane patches of guinea-pig submucosal neurones. *J. Physiol. (London).*, 445, 581–599.

Siegelbaum, S. A., Camardo, J. S. and Kandel, E. (1982) Serotonin and cyclic AMP close single K$^+$ channels in Aplysia sensory neurones. *Nature.*, 229, 413–417.

Siesjö, B. K., von Hanwehr, R., Nerglius, G., Nevander, G. and Ingvar, M. (1985) Extra- and intracellular pH in the brain during seizures and in the recovery period following the arrest of seizure activity. *J Cereb. Blood Flow Metab.*, 5, 47–57.

Takumi, T., Ohkubo, H. and Nakanishi, S. (1988) Cloning of a membrane protein that induces a slow voltage-gated potassium current. *Science.*, 242, 1042–1045.

Yamamoto, F., Borgula, G. A. and Steinberg, R. H. (1992) Effects of light and darkness on pH outside rod photoreceptors in the cat retina. *Exp. Eye Res.*, 54, 685–697.

While present invention has been described with reference to specific embodiments thereof, it will be appreciated that numerous variations, modifications, and embodiments are possible, and accordingly, all such variations, modifications and embodiments are to be regarded as being within the spirit and scope of the present invention.

What is claimed is:

1. An isolated and purified nucleic acid molecule coding for a protein capable of forming a potassium (K$^+$) ion channel, comprising two P domains and three or four transmembrane segments.

2. The nucleic acid molecule of claim 1 coding for a protein wherein the number of P domains is two and the number of transmembrane segments is four.

3. The nucleic acid molecule of claim 1 which is human.

4. The nucleic acid molecule of claim 1 which is a cDNA copy of a 2.6 kilobase transcript expressed at high levels in the pancreas and placenta, and at lower levels in the brain, lung, prostate, heart, kidney, uterus small intestine and colon.

5. The nucleic acid sequence of claim 1 which codes for a protein which comprises the sequence represented by SEQ ID NO:4.

6. The isolated and purified nucleic acid sequence of claim 1 which codes for a protein which comprises the sequence represented by SEQ ID NO:4 or a sequence having the equivalent function of being capable of forming a potassium (K$^+$) ion channel which comprises two P domains and four transmembrane segments.

7. An isolated and purified nucleic acid sequence of claim 2 which comprises an open reading frame (ORF) of 1185 nucleotides.

8. The isolated and purified nucleic acid sequence of claim 7 which is human.

9. A self replicating vector comprising the nucleic acid molecule of claim 1.

10. A cell transformed with the vector of claim 9, which cell is selected from the group consisting of prokaryotes and eukaryotes.

11. The transformed cell of claim 10 which is a yeast, insect cell, plant cell or mammalian cell.

12. The transformed cell of claim 10 which is a bacterium.

13. A method for the expression and isolation of a potassium transport channel encoded by a nucleic acid molecule according to claim 1 in a competent host cell comprising transferring a self-replicating vector including said nucleic acid molecule into a competent host cell, culturing said host cell under conditions allowing the production of the potassium transport channel, and isolating and purifying the polypeptide comprising the potassium transport channel.

* * * * *